United States Patent [19]

Barnes et al.

[11] Patent Number: 5,817,691
[45] Date of Patent: Oct. 6, 1998

[54] ARYLTHIO, -SULFINYL AND -SULFONYL PYRROLE INSECTICIDAL AGENTS

[75] Inventors: Keith Douglas Barnes, Newtown; Robert Eugene Diehl; Susan Hensen Trotto, both of Yardley, all of Pa.; Yulin Hu, Plainsboro, N.J.

[73] Assignee: American Cyanamid Company, Madison, N.J.

[21] Appl. No.: 838,747

[22] Filed: Apr. 9, 1997

[51] Int. Cl.[6] .................. C07D 207/325; A61K 43/36
[52] U.S. Cl. .................. 514/424; 514/91; 514/92; 514/423; 548/541; 548/543; 548/560; 548/564
[58] Field of Search .................. 548/560, 562, 548/541, 543; 514/91, 424, 423, 92

[56] References Cited

U.S. PATENT DOCUMENTS

| | | | |
|---|---|---|---|
| 5,010,098 | 4/1991 | Brown et al. | 514/426 |
| 5,281,719 | 1/1994 | Kameswaran et al. | 548/560 |
| 5,306,827 | 4/1994 | Barnes et al. | 548/543 |
| 5,310,938 | 5/1994 | Brown et al. | 548/557 |
| 5,484,807 | 1/1996 | Barnes et al. | 514/424 |

FOREIGN PATENT DOCUMENTS

| | | |
|---|---|---|
| 2076937 | 3/1993 | Canada . |
| 0372982 | 6/1990 | European Pat. Off. . |

*Primary Examiner*—Johann Richter
*Assistant Examiner*—Ebenezer O. Sackey
*Attorney, Agent, or Firm*—Gregory M. Hill

[57] ABSTRACT

There are provided arylthio, -sulfinyl and -sulfonyl pyrrole compounds having the structural formula I

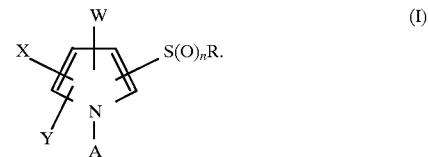

Further provided are compositions and methods comprising those compounds for the control of insects.

24 Claims, No Drawings

ARYLTHIO, -SULFINYL AND -SULFONYL PYRROLE INSECTICIDAL AGENTS

BACKGROUND OF THE INVENTION

Insects destroy growing and harvested crops. In the United States, agronomic crops must compete with thousands of insect species. In particular, tobacco budworms and southern armyworms are especially devastating to crops.

Tobacco budworms cause tremendous economic losses in agronomic crops. In particular, budworms devastate cotton crops by feeding on green bolls. Control of budworms is complicated by their resistance to many common insecticides, including organophosphates, carbamates and pyrethroids. Also, budworm larvae are difficult to control with currently available insecticides once they reach the third instar.

In spite of the commercial insecticides available today, damage to crops, both growing and harvested, caused by insects still occurs. Accordingly, there is ongoing research to create new and more effective insecticides.

Certain pyrrole compounds are known to possess insecticidal and acaricidal activity (see, e.g. U.S. Pat. Nos. 5,010,098; 5,281,719; 5,306,827 and 5,310,938; EP-A2-372982; and CA-A1-2,076,937). However, none of the pyrrole compounds disclosed in those patents and patent applications are within the scope of the present invention.

It is, therefore, an object of the present invention to provide compounds which are highly effective for controlling insects.

It is also an object of the present invention to provide a method for controlling insects.

It is a further object of this invention to provide a method for protecting growing plants from attack by insects.

Those and other objects of the present invention will become more apparent from the detailed description thereof set forth below.

SUMMARY OF THE INVENTION

The present invention describes arylthio, -sulfinyl and -sulfonyl pyrrole compounds which are useful for the control of insects and the protection of plants from attack by insects.

The arylthio, -sulfinyl and -sulfonyl pyrrole compounds of the present invention have the structural formula I

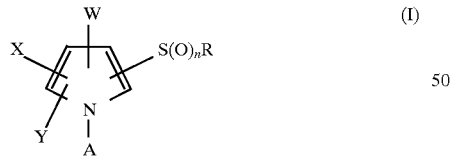

wherein

R and X are each independently phenyl optionally substituted with any combination of from one to five halogen, $NO_2$, CN, $C_1$–$C_4$alkyl, $C_1$–$C_4$haloalkyl, $C_1$–$C_4$alkoxy or $C_1$–$C_4$haloalkoxy groups;

n is an integer of 0, 1 or 2;

W is halogen, CN, $NO_2$ or $C_1$–$C_4$haloalkyl;

Y is hydrogen, halogen or $C_1$–$C_4$haloalkyl;

A is hydrogen, CN, $C(O)R_1$, $CHR_2NHC(O)R_3$, $CH_2SQ$, $CHR_4OC(O)$ $(CR_5R_6)_mQ$, $C_1$–$C_6$alkyl optionally substituted with
one to three halogen atoms,
one tri($C_1$–$C_4$alkyl)silyl,
one hydroxy,
one cyano,
one or two $C_1$–$C_4$alkoxy groups optionally substituted with one to three halogen atoms,
one $C_1$–$C_4$alkylthio,
one phenyl optionally substituted with one to three halogen atoms, one to three $C_1$–$C_4$alkyl groups or one to three $C_1$–$C_4$alkoxy groups,
one phenoxy group optionally substituted with one to three halogen atoms, one to three $C_1$–$C_4$alkyl groups or one to three $C_1$–$C_4$alkoxy groups,
one benzyloxy group optionally substituted on the phenyl ring with one to three halogen atoms, one to three $C_1$–$C_4$alkyl groups or one to three $C_1$–$C_4$alkoxy groups,
one $C_1$–$C_6$alkylcarbonyloxy group optionally substituted with one to three halogen atoms,
one $C_2$–$C_6$alkenylcarbonyloxy group optionally substituted with one to three halogen atoms,
one phenylcarbonyloxy group optionally substituted with one to three halogen atoms, one to three $C_1$–$C_4$alkyl groups or one to three $C_1$–$C_4$alkoxy groups,
one $C_1$–$C_6$alkoxycarbonyl group optionally substituted with one to three halogen atoms or one to three $C_1$–$C_4$alkoxy groups, or
one benzylcarbonyloxy group optionally substituted on the phenyl ring with one to three halogen atoms, one to three $C_1$–$C_4$alkyl groups or one to three $C_1$–$C_4$alkoxy groups,
$C_3$–$C_6$alkenyl optionally substituted with one to three halogen atoms or one phenyl group, or
$C_3$–$C_6$alkynyl optionally substituted with one to three halogen atoms or one phenyl group;

$R_1$ is $C_1$–$C_6$alkyl or $C_3$–$C_6$cycloalkyl each optionally substituted with
one to three halogen atoms,
one hydroxy,
one cyano,
one or two $C_1$–$C_4$alkoxy groups optionally substituted with one to three halogen atoms,
one $C_1$–$C_4$alkylthio,
one phenyl group optionally substituted with one to three halogen atoms, one to three $C_1$–$C_4$alkyl groups or one to three $C_1$–$C_4$alkoxy groups,
one phenoxy group optionally substituted with one to three halogen atoms, one to three $C_1$–$C_4$alkyl groups or one to three $C_1$–$C_4$alkoxy groups,
one benzyloxy group optionally substituted on the phenyl ring with one to three halogen atoms, one to three $C_1$–$C_4$alkyl groups or one to three $C_1$–$C_4$alkoxy groups,
one $C_1$–$C_6$alkylcarbonyloxy group optionally substituted with one to three halogen atoms,
one $C_2$–$C_6$alkenylcarbonyloxy group optionally substituted with one to three halogen atoms,
one phenylcarbonyloxy group optionally substituted with one to three halogen atoms, one to three $C_1$–$C_4$alkyl groups or one to three $C_1$–$C_4$alkoxy groups,
one $C_1$–$C_6$alkoxycarbonyl group optionally substituted with one to three halogen atoms or one to three $C_1$–$C_4$alkoxy groups, or
one benzyloxycarbonyl group optionally substituted on the phenyl ring with one to three halogen atoms, one to three $C_1$–$C_4$alkyl groups or one to three $C_1$–$C_4$alkoxy groups, $C_2$–$C_6$alkenyl optionally substituted with one to three halogen atoms or one phenyl group, $C_3$–$C_6$alkynyl optionally substituted with one to three halogen atoms or one phenyl group, phenyl optionally substituted with one or more halogen atoms, $C_1$–$C_4$alkyl groups, $C_1$–$C_4$alkoxy groups, phenoxy groups, $C_1$–$C_4$alkylthio groups, tri($C_1$–$C_4$alkyl)silyl groups, $C_1$–$C_4$alkylsulfinyl groups, $C_1$–$C_4$alkylsulfonyl groups, CN groups, $NO_2$ groups or $CF_3$ groups, phenoxy optionally substituted with one or more halogen atoms, $C_1$–$C_4$alkyl groups, $C_1$–$C_4$alkoxy groups, $C_1$–$C_4$alkylthio groups, tri($C_1$–$C_4$alkyl)silyl groups, $C_1$–$C_4$alkylsulfinyl groups, $C_1$–$C_4$alkylsulfonyl groups, CN groups, $NO_2$ groups or $CF_3$ groups, 1- or 2-naphthyl, 2-, 3- or 4-pyridyl optionally substituted with one to three halogen atoms, $C_1$–$C_6$alkoxy optionally substituted with one to three halogen atoms, or $C_2$–$C_6$alkenyloxy optionally substituted with one to three halogen atoms;

$R_2$ is hydrogen or $C_1$–$C_4$alkyl;

$R_3$ is $C_1$–$C_6$alkyl optionally substituted with one to three halogen atoms, phenyl optionally substituted with one to three halogen atoms, CN groups, $NO_2$ groups, $C_1$–$C_4$alkyl groups, $C_1$–$C_4$alkoxy groups or $CF_3$ groups, 2- or 3-thienyl, or 2- or 3-furyl;

Q is $$\overset{A_1}{\underset{}{C}}-R_7, \overset{A_1}{\underset{}{C}}-OR_8, \overset{A_1}{\underset{}{C}}-NR_9R_{10}, \overset{A_1}{\underset{}{P}}-(OR_{11})_2, \overset{NR_{12}}{\underset{}{C}}-NR_{13}R_{14},$$

$$\overset{NR_{12}}{\underset{}{C}}-A_1R_{15}, \quad \begin{array}{c} A_1 \\ \diagup \diagdown \\ N \\ R_{17} \end{array} R_{16}, \quad \begin{array}{c} H \\ N \\ \diagup \diagdown \\ N \\ R_{17} \end{array} R_{16}, CN,$$

$C_1$–$C_6$alkyl optionally substituted with one or more halogen atoms, CN groups or phenyl groups, or phenyl optionally substituted with one or more halogen atoms, $C_1$–$C_4$alkyl groups, $C_1$–$C_4$alkoxy groups, CN groups, $NO_2$ groups, $CF_3$ groups or $NR_{18}R_{19}$ groups;

$A_1$ is O or S;

$R_7$ is $C_1$–$C_6$alkyl or phenyl;

$R_8$ is $C_1$–$C_6$alkyl;

$R_9$ and $R_{10}$ are each independently hydrogen, $C_1$–$C_6$alkyl or may be taken together with the atom to which they are attached to form a 5- to 7-membered heterocyclic ring;

$R_{11}$ is $C_1$–$C_4$alkyl;

$R_{12}$ is hydrogen, $C_1$–$C_4$alkyl or may be taken together with either $R_{13}$ or $R_{15}$ and the atoms to which they are attached to form a 5- to 7-membered heterocyclic ring optionally substituted with one or two $C_1$–$C_4$alkyl groups;

$R_{13}$ and $R_{14}$ are each independently hydrogen or $C_1$–$C_4$alkyl;

$R_{15}$ is $C_1$–$C_4$alkyl or when taken together with $R_{12}$ and the atoms to which they are attached may form a 5- to 7-membered heterocyclic ring optionally substituted with one or two $C_1$–$C_4$alkyl groups;

$R_{16}$ and $R_{17}$ are each independently hydrogen or $C_1$–$C_4$alkyl or when taken together may form a ring wherein $R_{16}R_{17}$ is represented by —CH=CH—CH=CH—;

$R_{18}$ and $R_{19}$ are each independently hydrogen or $C_1$–$C_4$alkyl;

$R_4$ is hydrogen or $C_1$–$C_4$alkyl;

$R_5$ and $R_6$ are each independently hydrogen, $C_1$–$C_6$alkyl optionally substituted with one or more halogen atoms, $C_1$–$C_6$alkoxy optionally substituted with one or more halogen atoms, $C_1$–$C_6$alkylthio optionally substituted with one or more halogen atoms, or phenyl optionally substituted with one or more halogen atoms, $NO_2$ groups;

CN groups, $C_1$–$C_4$alkyl groups optionally substituted with one or more halogen atoms, or $C_1$–$C_4$alkoxy groups optionally substituted with one or more halogen atoms, or when $R_5$ and $R_6$ are taken together with the atom to which they are attached may form a $C_3$–$C_6$cycloalkyl group optionally substituted with one to three $C_1$–$C_4$alkyl groups, $C_2$–$C_6$alkenyl groups or phenyl groups, or $R_5$ or $R_6$ may be taken together with $R_{20}$ and the atoms to which they are attached to form a 4- to 7-membered heterocyclic ring;

m is an integer of 0, 1, 2, 3 or 4;

$Q_1$ is $A_2R_{20}$, $$\overset{O}{\underset{}{P}}-(OR_{21})_2,$$

$NR_{22}R_{23}$, $CR_{24}R_{25}C(O)R_{26}$, or $C_3$–$C_6$cycloalkyl optionally substituted with one or more $C_1$–$C_6$alkyl groups, $C_2$–$C_6$alkenyl groups, or phenyl groups optionally substituted with one or more halogen atoms, $NO_2$ groups, CN groups, $C_1$–$C_4$alkyl groups optionally substituted with one or more halogen atoms, or $C_1$–$C_4$alkoxy groups optionally substituted with one or more halogen atoms;

$A_2$ is O or $S(O)_p$;

p is an integer of 0, 1 or 2;

$R_{20}$ is hydrogen, $C_1$–$C_6$alkyl, $C_2$–$C_6$alkenyl, $C_2$–$C_6$alkynyl, phenyl optionally substituted with one or more halogen atoms, $NO_2$ groups, CN groups, $C_1$–$C_4$alkyl groups optionally substituted with one or more halogen atoms, $C_1$–$C_4$alkoxy groups optionally substituted with one or more halogen atoms, $C(O)R_{27}$ provided p is 0, $C(O)R_{28}$ provided p is 0, $(CH_2CH_2O)_qR_{27}$, or

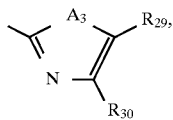

or $R_{20}$ may be taken together with either $R_5$ or $R_6$ and the atoms to which they are attached to form a 4- to 7-membered heterocyclic ring;

$A_3$ is O or S;

$R_{27}$ is $C_1$–$C_6$alkyl,
$C_2$–$C_6$alkenyl,
$C_2$–$C_6$alkynyl, or
phenyl optionally substituted with one or more
halogen atoms,
$NO_2$ groups,
CN groups,
$C_1$–$C_4$alkyl groups optionally substituted with one or more halogen atoms, or
$C_1$–$C_4$alkoxy groups optionally substituted with one or more halogen atoms;

q is an integer of 1, 2 or 3;

$R_{28}$ is $OR_{31}$ or $NR_{32}R_{33}$;

$R_{31}$ is $C_1$–$C_6$alkyl or
phenyl optionally substituted with one or more
halogen atoms,
$NO_2$ groups,
CN groups,
$C_1$–$C_4$alkyl groups optionally substituted with one or more halogen atoms, or
$C_1$–$C_4$alkoxy groups optionally substituted with one or more halogen atoms;

$R_{32}$ and $R_{33}$ are each independently hydrogen or $C_1$–$C_4$alkyl;

$R_{29}$ and $R_{30}$ are each independently hydrogen or $C_1$–$C_4$alkyl, or when taken together may form a ring wherein $R_{29}R_{30}$ is represented by —CH=CH—CH=CH—;

$R_{21}$ is $C_1$–$C_4$alkyl;

$R_{22}$ is hydrogen,
$C_1$–$C_6$alkyl,
$C_2$–$C_6$alkenyl,
$C_2$–$C_6$alkynyl, or
phenyl optionally substituted with one or more
halogen atoms,
$NO_2$ groups,
CN groups,
$C_1$–$C_4$alkyl groups optionally substituted with one or more halogen atoms, or
$C_1$–$C_4$alkoxy groups optionally substituted with one or more halogen atoms, or $R_{22}$ may be taken together with either $R_5$ or $R_6$ and the atoms to which they are attached to form a 4- to 7-membered heterocyclic ring;

$R_{23}$ is hydrogen,
$C_1$–$C_6$alkyl,
$C_2$–$C_6$alkenyl,
$C_2$–$C_6$alkynyl,
phenyl optionally substituted with one or more
halogen atoms,
$NO_2$ groups,
CN groups,
$C_1$–$C_4$alkyl groups optionally substituted with one or more halogen atoms, or
$C_1$–$C_4$alkoxy groups optionally substituted with one or more halogen atoms,
$C(A_4)R_{34}$,
CN,
$SO_2R_{35}$, or
$C(O)CHR_{36}NHR_{37}$;

$A_4$ is O or S;

$R_{34}$ is $OR_{38}$, $CO_2R_{38}$, $NR_{39}R_{40}$,
$C_1$–$C_6$alkyl optionally substituted with one to three halogen atoms,
$C_2$–$C_6$alkenyl,
$C_2$–$C_6$alkynyl, or
phenyl optionally substituted with one or more
halogen atoms,
$NO_2$ groups,
CN groups,
$C_1$–$C_4$alkyl groups optionally substituted with one or more halogen atoms, or
$C_1$–$C_4$alkoxy groups optionally substituted with one or more halogen atoms;

$R_{38}$ is $C_1$–$C_6$alkyl optionally substituted with one phenyl group, or
phenyl optionally substituted with one or more
halogen atoms,
$NO_2$ groups,
CN groups,
$C_1$–$C_4$alkyl groups optionally substituted with one or more halogen atoms, or
$C_1$–$C_4$alkoxy groups optionally substituted with one or more halogen atoms;

$R_{39}$ and $R_{40}$ are each independently hydrogen or $C_1$–$C_4$alkyl;

$R_{35}$ is $NR_{41}R_{42}$,
$C_1$–$C_6$alkyl,
$C_2$–$C_6$alkenyl,
$C_2$–$C_6$alkynyl, or
phenyl optionally substituted with one or more
halogen atoms,
$NO_2$ groups,
CN groups,
$C_1$–$C_4$alkyl groups optionally substituted with one or more halogen atoms, or
$C_1$–$C_4$alkoxy groups optionally substituted with one or more halogen atoms;

$R_{41}$ and $R_{42}$ are each independently hydrogen or $C_1$–$C_4$alkyl;

$R_{36}$ is hydrogen,
$C_1$–$C_4$alkyl optionally substituted with
one hydroxy group,
one $SR_{43}$ group,
one $C(O)NH_2$ group,
one $NH_2$ group,
one $NHC(=NH)NH_2$ group,
one $CO_2H$ group,
one phenyl group optionally substituted with one hydroxy group,
one 3-indolyl group or
one 4-imidazolyl group;

$R_{43}$ is hydrogen or $C_1$–$C_4$alkyl;

$R_{37}$ is $C(A_4)R_{44}$;

$R_{44}$ is $C_1$–$C_6$alkyl optionally substituted with one or more
halogen atoms,
$C_2$–$C_6$alkoxyalkyl,
$C_1$–$C_6$alkylthio,
phenyl optionally substituted with one or more
halogen atoms, $NO_2$ groups, $CN$ groups, $C_1-C_4$alkyl groups optionally substituted with one or more halogen atoms, or $C_1-C_4$alkoxy groups optionally substituted with one or more halogen atoms, $OR_{38}$, $CO_2R_{38}$ or $NR_{39}R_{40}$;

$R_{24}$ and $R_{25}$ are each independently hydrogen, $C_1-C_6$alkyl optionally substituted with one or more halogen atoms, $C_1-C_6$alkoxy optionally substituted with one or more halogen atoms, $C_1-C_6$alkylthio optionally substituted with one or more halogen atoms, phenyl optionally substituted with one or more halogen atoms, $CN$ groups, $NO_2$ groups, $C_1-C_4$alkyl groups optionally substituted with one or more halogen atoms, or $C_1-C_4$alkoxy groups optionally substituted with one or more halogen atoms, or when $R_{24}$ and $R_{25}$ are taken together with the atom to which they are attached may form a $C_3-C_6$cycloalkyl group optionally substituted with one to three $C_1-C_4$alkyl groups, $C_2-C_6$alkenyl groups or phenyl groups;

$R_{26}$ is $OR_{45}$, $NR_{41}R_{42}$, $C_1-C_4$alkyl or phenyl optionally substituted with one or more halogen atoms, $CN$ groups, $NO_2$ groups, $C_1-C_4$alkyl groups optionally substituted with one or more halogen atoms, or $C_1-C_4$alkoxy groups optionally substituted with one or more halogen atoms; and $R_{45}$ is $C_1-C_4$alkyl or phenyl optionally substituted with one or more halogen atoms, $CN$ groups, $NO_2$ groups, $C_1-C_4$alkyl groups optionally substituted with one or more halogen atoms, or $C_1-C_4$alkoxy groups optionally substituted with one or more halogen atoms.

This invention also relates to compositions containing those compounds and methods for using those compounds and compositions. Advantageously, it has been found that the arylthio, -sulfinyl and -sulfonyl pyrrole compounds of the present invention, and compositions containing them, are useful for the control of insects and the protection of plants from attack by insects. The compounds of the present invention are especially useful for the control of tobacco budworms and southern armyworms.

DETAILED DESCRIPTION OF THE INVENTION

The present invention provides a method for controlling insects which comprises contacting said insects, their breeding grounds, food supply or habitat with an insecticidally effective amount of a formula I, arylthio, -sulfinyl or -sulfonyl pyrrole compound.

The present invention also provides a method for protecting growing plants from attack by insects which comprises applying to the foliage of said plants or to the soil or water in which they are growing an insecticidally effective amount of a formula I, arylthio, -sulfinyl or -sulfonyl pyrrole compound.

The arylthio, -sulfinyl and -sulfonyl pyrrole compounds of the present invention have the structural formula I

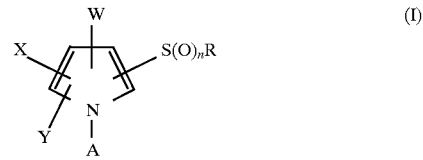

wherein A, R, W, X, Y and n are as described hereinabove for formula I.

Preferred formula I arylthio, -sulfinyl and -sulfonyl pyrrole compounds of the present invention are those wherein R and X are each independently phenyl optionally substituted with any combination of from one to three halogen, $NO_2$, $CN$, $C_1-C_4$alkyl, $C_1-C_4$haloalkyl, $C_1-C_4$alkoxy or $C_1-C_4$haloalkoxy groups;

n is an integer of 0, 1 or 2;

W is Cl, Br, CN, $NO_2$ or $C_1-C_4$haloalkyl;

Y is hydrogen, Cl, Br or $C_1-C_4$haloalkyl;

A is hydrogen, CN, $C(O)R_1$ or $C_1-C_4$alkyl optionally substituted with one to three halogen atoms, one cyano, one $C_1-C_4$alkoxy group, one $C_1-C_6$alkylcarbonyloxy group, one phenylcarbonyloxy group optionally substituted with one to three halogen atoms or one $C_1-C_4$alkyl group, or one benzylcarbonyloxy group; and $R_1$ is phenyl optionally substituted with one to three halogen atoms, one or two $C_1-C_4$alkyl groups, one or two $C_1-C_4$alkoxy groups, one CN group, one $NO_2$ group or one $CF_3$ group.

More preferred insecticidal agents of the present invention are those having the structural formula II

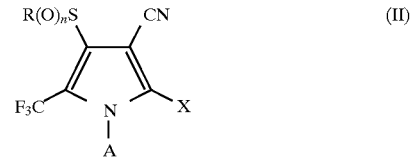

wherein

R and X are each independently phenyl optionally substituted with any combination of from one to three halogen, $NO_2$ or $CF_3$ groups;

n is an integer of 0, 1 or 2; and

A is hydrogen or $C_1-C_4$alkyl substituted with one $C_1-C_4$alkoxy group.

Another group of more preferred insecticidal agents of this invention are those having the structural formula III

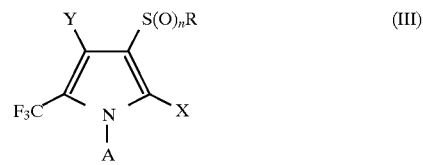

wherein

R and X are each independently phenyl optionally substituted with any combination of from one to three halogen, $NO_2$ or $CF_3$ groups;

n is an integer of 0, 1 or 2;

Y is Cl or Br; and

A is hydrogen or $C_1$–$C_4$alkyl substituted with one $C_1$–$C_4$alkoxy group.

A third group of more preferred arylthio, -sulfinyl and -sulfonyl pyrrole compounds of the present invention are those having the structural formula IV

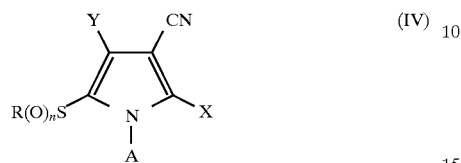

wherein

R and X are each independently phenyl optionally substituted with any combination of from one to three halogen, $NO_2$ or $CF_3$ groups;

n is an integer of 0, 1 or 2;

Y is hydrogen, Cl or Br; and

A is hydrogen or $C_1$–$C_4$alkyl substituted with one $C_1$–$C_4$alkoxy group.

Formula I compounds of the present invention which are particularly effective insecticidal agents include 2-(p-chlorophenyl)-4-[(3,4-dichlorophenyl)thio]-5-(trifluoromethyl)pyrrole-3-carbonitrile;

2-(p-chlorophenyl)-4-[(p-chlorophenyl)thio]-5-(trifluoromethyl)pyrrole-3-carbonitrile;

3-bromo-4-[(3-chloro-4-fluorophenyl)sulfonyl]-5-(p-chlorophenyl)-2-(trifluoromethyl)pyrrole;

3-bromo-5-(p-chlorophenyl)-4-[(p-chlorophenyl)sulfonyl]-2-(trifluoromethyl)pyrrole;

4-bromo-2-(p-chlorophenyl)-5-[(p-chlorophenyl)sulfonyl]pyrrole-3-carbonitrile;

2-(p-chlorophenyl)-5-[(3,4-dichlorophenyl)sulfonyl]pyrrole-3-carbonitrile; and 2-(p-chlorophenyl)-5-[(3,4-dichlorophenyl)sulfonyl]-1-(ethoxymethyl)pyrrole-3-carbonitrile, among others.

Exemplary of halogen hereinabove are fluorine, chlorine, bromine and iodine. The terms "$C_1$–$C_4$haloalkyl" and "$C_1$–$C_4$haloalkoxy" are defined as a $C_1$–$C_4$alkyl group and a $C_1$–$C_4$alkoxy group substituted with one or more halogen atoms, respectively.

Advantageously, it has been found that the formula I compounds of the present invention are especially useful for the control of tobacco budworms and southern army-worms.

Formula I compounds wherein A is hydrogen and R, W, X, Y and n are as described hereinabove for formula I may be prepared by reacting a substituted pyrrole of formula V with an arylsulfenyl halide of formula VI optionally in the presence of a base to form an arylthio pyrrole of formula Ia, and optionally oxidizing the arylthio pyrrole with a suitable oxidizing agent such as hydrogen peroxide, 3-chloroperoxybenzoic acid, potassium peroxymonosulfate and the like to obtain an arylsulfinyl pyrrole of formula Ib or an arylsulfonyl pyrrole of formula Ic. The reaction scheme is shown below in Flow Diagram I.

FLOW DIAGRAM I

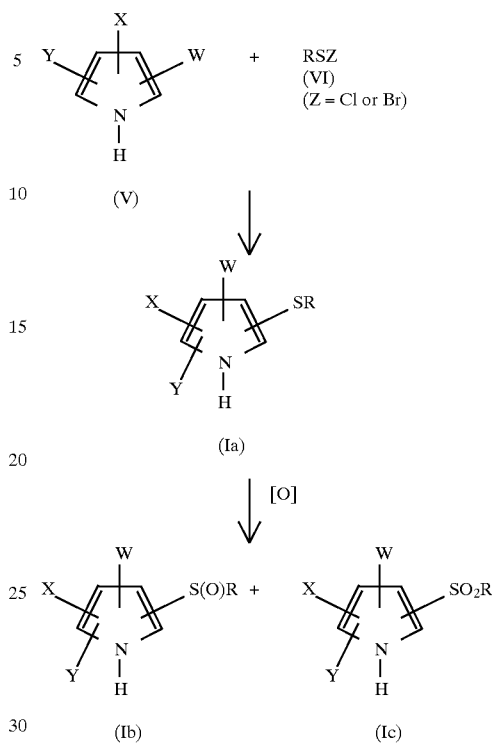

1-Substituted formula I compounds may be prepared by reacting a formula I compound wherein A is hydrogen with an alkylating or acylating agent in the presence of an alkali metal alkoxide or hydride. For example, a formula I compound wherein A is hydrogen and R, W, X, Y and n are as described for formula I above is reacted with an alkylating agent such as a $C_1$–$C_6$alkylhalide in which the alkyl group is straight or branched and is optionally substituted with one to three halogen atoms, one hydroxy, one cyano, one $C_1$–$C_4$alkoxy, one $C_1$–$C_4$alkylthio, one phenyl optionally substituted with one to three halogen atoms, or one benzyloxy group optionally substituted with one to three halogen atoms, and an alkali metal alkoxide such as sodium or potassium tert-butoxide. That reaction provides an arylthio, -sulfinyl or -sulfonyl pyrrole having the same substituents as the starting material, but in addition is substituted on the nitrogen atom with a $C_1$–$C_6$alkyl group optionally substituted as described above. The reaction scheme is shown in Flow Diagram II.

FLOW DIAGRAM II

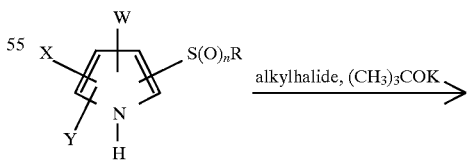

-continued
FLOW DIAGRAM II

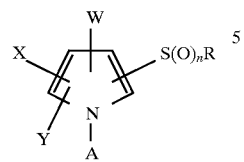

wherein R, W, X, Y and n are as described for formula I above and A is $C_1$–$C_6$alkyl optionally substituted as described above. In a similar reaction, cyanogen bromide is substituted for the alkylhalide and provides a formula I arylthio, -sulfinyl or -sulfonyl pyrrole wherein A is cyano.

Advantageously, the above-described alkylation procedure may also be applied for the preparation of formula I compounds wherein A is $C_3$–$C_6$alkenyl or $C_3$–$C_6$alkynyl. This is achieved by substituting a $C_3$–$C_6$alkenyl halide or $C_3$–$C_6$alkynyl halide for the $C_1$–$C_6$alkyl halide used in the above-described reaction.

In a similar manner, 1-acylated arylthio, -sulfinyl and -sulfonyl pyrroles may be prepared by reacting a formula I compound wherein A is hydrogen with an acylating agent in the presence of an alkali metal alkoxide. Acylating agents such as optionally substituted $C_1$–$C_6$alkyl and $C_2$–$C_6$alkenyl acid chlorides, an optionally substituted benzoyl chloride, an optionally substituted phenylchloroformate, optionally substituted $C_1$–$C_6$alkyl- and $C_2$–$C_6$alkenylchloroformates, an N-substituted carbamoyl chloride and the like may be used. The reaction is shown in Flow Diagram III.

FLOW DIAGRAM III

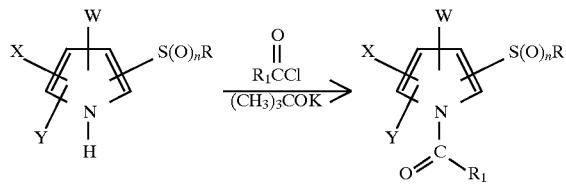

Formula I compounds wherein A is $CH_2SQ$ may be prepared by reacting a formula I compound wherein A is chloromethyl with an alkali metal salt of an SQ compound in the presence of a base. And formula I compounds wherein A is $CHR_2NHC(O)R_3$ may be prepared as shown below in Flow Diagram IV.

FLOW DIAGRAM IV

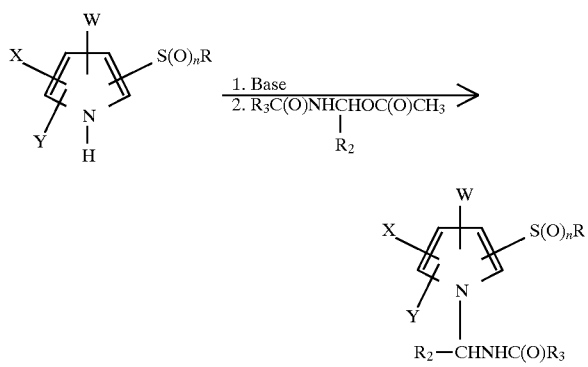

Advantageously, 1-halomethyl pyrroles of this invention may be prepared by reacting a formula I compound wherein A is $CH(R_2)NHC(O)R_3$ with a phosphorus oxyhalide compound such as phosphorus oxychloride. The reaction scheme is shown in Flow Diagram V.

FLOW DIAGRAM V

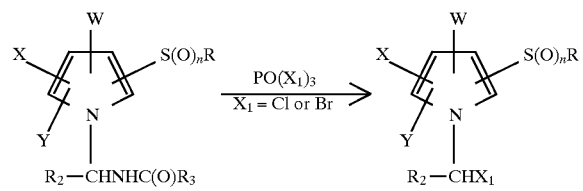

Formula I compounds wherein A is $CHR_4OC(O)(CR_5R_6)_mQ_l$ may be prepared by reacting a 1-halomethyl pyrrole of this invention with a $Q_1(CR_5R_6)_mCO_2H$ compound in the presence of a base such as sodium hydroxide. The reaction is shown in Flow Diagram VI.

FLOW DIAGRAM VI

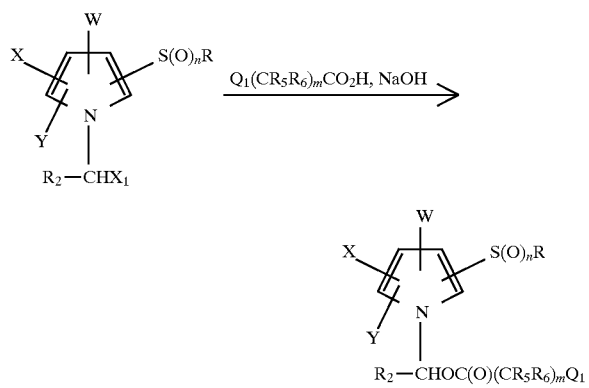

Starting formula V pyrrole compounds are known in the art (see, e.g., U.S. Pat. No. 5,010,098; U.S. Pat. No. 5,281,719 and CA-Al-2,076,937).

The arylthio, -sulfinyl and -sulfonyl pyrrole compounds of the present invention are effective for controlling undesirable insect species. Those compounds are also effective for protecting growing or harvested crops from attack by insects.

Insects which may be controlled by the formula I compounds of this invention include Lepidoptera such as tobacco budworms, cabbage loopers, cotton boll worms, beet armyworms, southern armyworms and diamondback moths; Homoptera such as aphids, leaf hoppers, plant hoppers and white flies; Thysanoptera such as thrips; Coleoptera such as boll weevils, Colorado potato beetles, southern corn rootworms and mustard beetles; and Orthoptera such as locusts, crickets, grasshoppers and cockroaches. The compounds of the present invention are especially effective against Lepidoptera such as tobacco budworms and southern armyworms.

Surprisingly, it has been found that, in general, the compounds of the present invention are not effective for the control of mites. That property makes the compounds of the present invention especially suitable for use in integrated pest management systems which utilize predatory mites.

In practice generally about 10 ppm to about 10,000 ppm and preferably about 100 ppm to about 5,000 ppm of a formula I arylthio, -sulfinyl or -sulfonyl pyrrole, dispersed in water or another liquid carrier, is effective when applied to the plants, the crops or the soil in which said crops are growing to protect said crops from attack by insects.

The arylthio, -sulfinyl and -sulfonyl pyrrole compounds of this invention are also effective for controlling insects when applied to the foliage of plants and/or to the soil or water in which said plants are growing in sufficient amount to provide a rate of about 0.1 kg/ha to 4.0 kg/ha of active ingredient.

While the compounds of this invention are effective for controlling insects when employed alone, they may also be used in combination with other biological chemicals, including other insecticides. For example, the formula I compounds of this invention may be used effectively in conjunction or combination with pyrethroids, phosphates, carbamates, cyclodienes, endotoxin of bacillus thuringiensis (Bt), formamidines, phenol tin compounds, chlorinated hydrocarbons, benzoylphenyl ureas and the 1like.

The compounds of this invention may be formulated as emulsifiable concentrates, flowable concentrates or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations include the compounds of the invention admixed with agronomically acceptable inert, solid or liquid carriers.

In order to facilitate a further understanding of the invention, the following examples are presented primarily for the purpose of illustrating more specific details thereof. The examples generally utilize the above reaction schemes and also provide further means for preparing compounds of the present invention. The invention should not be deemed limited by the examples as the full scope of the invention is defined in the claims.

EXAMPLE 1

Preparation of 2-(p-Chlorophenyl)-3-[(p-chlorophenyl)thio]-5-(trifluoromethyl)pyrrole

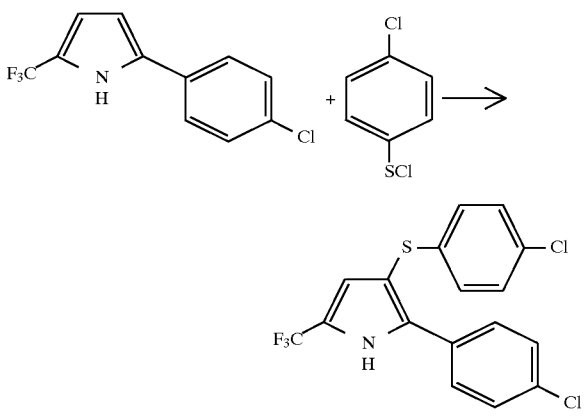

A solution of p-chlorophenylsulfenyl chloride (0.80 g, 4.48 mmol) in methylene chloride is added dropwise over 20 minutes to a stirred solution of 2-(p-chlorophenyl)-5-trifluoromethylpyrrole (1.0 g, 4.07 mmol) in methylene chloride. The reaction mixture is stirred at room temperature for 90 minutes, diluted with methylene chloride, washed sequentially with water and brine, dried over anhydrous magnesium sulfate and concentrated in vacuo to obtain a residue. Flash column chromatography of the residue using silica gel and a 1:10 ethyl acetate/hexanes solution gives the title product as an off-white solid (0.96 g, mp 39°–54° C.).

Using essentially the same procedure, the following compounds are obtained:

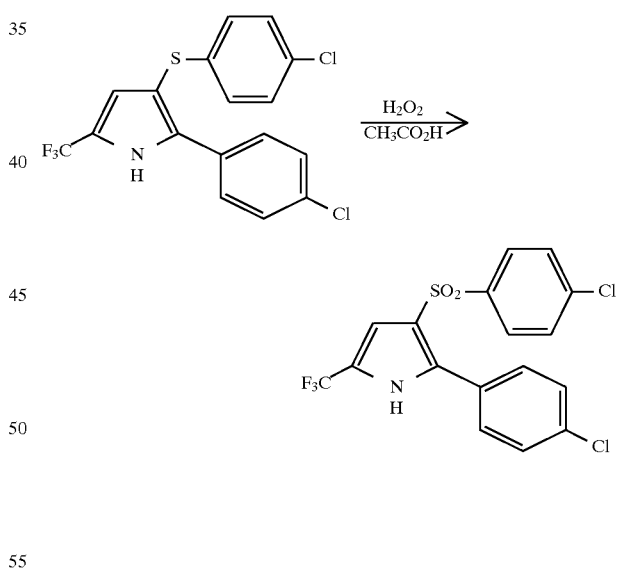

| L  | M   | State/mp °C. |
|----|-----|--------------|
| H  | H   | syrup        |
| Cl | F   | syrup        |
| H  | NO$_2$ | 112       |

EXAMPLE 2

Preparation of 2-(p-Chlorophenyl)-3-[(p-chlorophenylsulfonyl]-5-(trifluoromethyl)pyrrole A solution of 2-(p-chlorophenyl)-3-[(p-chlorophenyl)thio]-5-(trifluoromethyl)pyrrole (1.0 g, 2.58 mmol) and 30% hydrogen peroxide solution (0.88 g, 7.73 mmol) in acetic acid is stirred at room temperature for 1 hour, stirred at 75° C. for 2 hours, cooled to room temperature and poured into water. The resultant aqueous mixture is filtered to obtain the title product as a white solid (0.62 g, mp 200°–206° C.).

Using essentially the same procedure, the following compounds are obtained:

| Y | mp °C. |
|---|---|
| H | 153–156 |
| Br | 167–169 |

| L | M | State/mp °C. |
|---|---|---|
| H | Cl | syrup |
| H | H | syrup |
| Cl | F | 181–184 |

EXAMPLE 3

Preparation of 3-Bromo-5-(p-chlorophenyl)-4-[(p-chlorophenyl)sulfonyl]-2-(trifluoromethyl)pyrrole

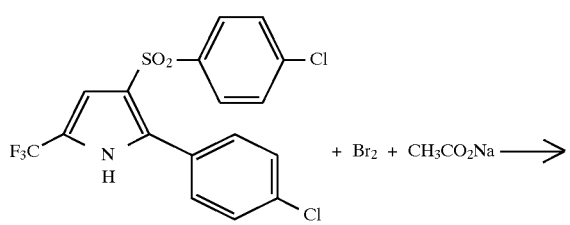

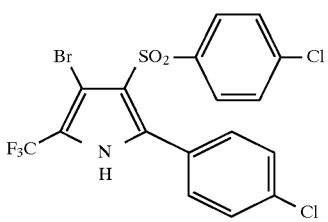

A solution of 2-(p-chlorophenyl)-3-[(p-chlorophenyl)sulfonyl]-5-(trifluoromethyl)pyrrole (2.15 g, 5.12 mmol), bromine (0.29 mL, 5.63 mmol) and sodium acetate (0.46 g, 5.63 mmol) in acetic acid is stirred at room temperature for 4 hours, treated with additional bromine (3 drops), stirred overnight at room temperature and poured into water. The resultant aqueous mixture is filtered to obtain a solid. Flash column chromatography of the solid using silica gel and a 1:5 ethyl acetate/hexanes solution gives the title product as a white solid (1.88 g, mp >230° C.).

Using essentially the same procedure, the following compounds are obtained:

EXAMPLE 4

Preparation of 3-Bromo-5-(p-chlorophenyl)-4-[(p-chlorophenyl)sulfonyl]-1-(ethoxymethyl)-2-(trifluoromethyl)pyrrole

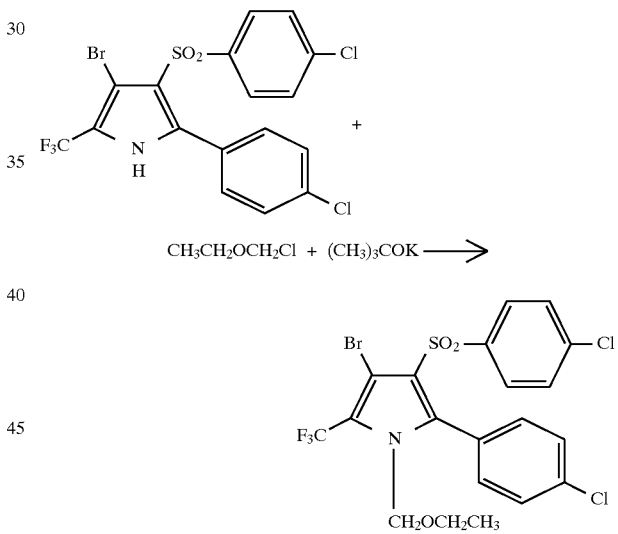

A solution of 3-bromo-5-(p-chlorophenyl)-4-[(p-chlorophenyl)sulfonyl]-2-(trifluoromethyl)pyrrole (0.92 g, 1.84 mmol) and potassium tert-butoxide (0.26 g, 2.21 mmol) in tetrahydrofuran is stirred at room temperature for 5 minutes, treated with a solution of chloromethyl ethyl ether (0.21 g, 2.21 mmol) in tetrahydrofuran, stirred at room temperature overnight, diluted with ethyl acetate, washed sequentially with water and brine, dried over anhydrous magnesium sulfate and concentrated in vacuo to give the title product as a white solid (0.98 g, mp 107°–112° C.).

Using essentially the same procedure, the following compounds are obtained:

| Y | L | M | n | State/mp °C. |
|---|---|---|---|---|
| H | H | Cl | 1 | 95–100 |
| H | H | Cl | 2 | 108–110 |
| Br | H | Cl | 1 | syrup |
| H | H | H | 0 | syrup |
| H | H | H | 1 | syrup |
| Br | H | H | 0 | 96–98 |
| H | H | H | 2 | syrup |
| Cl | H | H | 0 | syrup |
| H | Cl | F | 0 | 56–58 |
| H | Cl | F | 1 | syrup |
| Br | Cl | F | 1 | 111–114 |
| H | H | $NO_2$ | 0 | 76–77 |
| Br | Cl | F | 0 | 80–83 |

| Y | L | M | mp °C. |
|---|---|---|---|
| H | H | H | 141–144 |
| Br | H | H | 96–98 |
| Br | H | Cl | 162–164 |
| Cl | H | H | 151–153 |
| H | Cl | F | 180–183 |
| Br | Cl | F | 169–172 |

EXAMPLE 5

Preparation of 2-(p-Chlorophenyl)-3-[(p-chlorophenyl)sulfinyl]-5-(trifluoromethyl)pyrrole

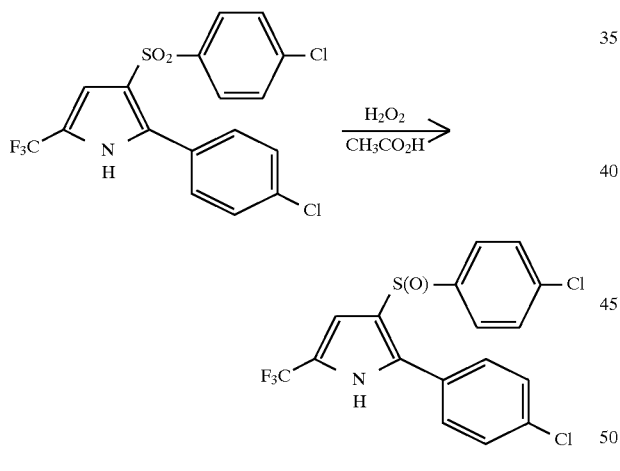

A solution of 2-(p-chlorophenyl)-3-[(p-chlorophenyl)thio]-5-(trifluoromethyl)pyrrole (2.57 g, 6.6 mmol) and 30% hydrogen peroxide solution (0.83 g, 7.3 mmol) in acetic acid is stirred at room temperature overnight and poured into water. The resultant aqueous mixture is filtered to obtain a solid. A solution of the solid in methylene chloride is washed with brine, dried over anhydrous magnesium sulfate and concentrated in vacuo to obtain a residue. Flash column chromatography of the residue using silica gel and a 1:3 ethyl acetate/hexanes solution gives the title product as a white solid (1.75 g, mp 174°–176° C.)

Using essentially the same procedure, the following compounds are obtained:

EXAMPLE 6

Preparation of 3-Chloro-5-(p-chlorophenyl)-4-(phenylthio)-2-(trifluoromethyl)pyrrole

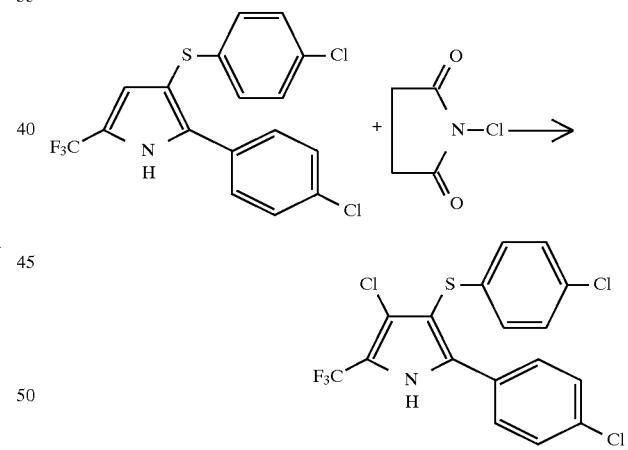

N-Chlorosuccinimide (0.734 g, 5.5 mmol) is added to a solution of 2-(p-chlorophenyl)-3-(phenylthio)-5-(trifluoromethyl)pyrrole (1.77 g, 5 mmol) in tetrahydrofuran. The reaction mixture is stirred overnight at room temperature, concentrated in vacuo, diluted with carbon tetrachloride and filtered. The resultant filtrate is concentrated in vacuo to obtain a residue. Flash column chromatography of the residue using silica gel and a 1:10 ethyl acetate/hexanes solution gives the title product as a yellow syrup which is identified by $^1H$ NMR spectral analysis.

EXAMPLE 7

Preparation of 2-(p-Chlorophenyl)-5-[(p-nitrophenyl)thiol pyrrole-3-carbonitrile

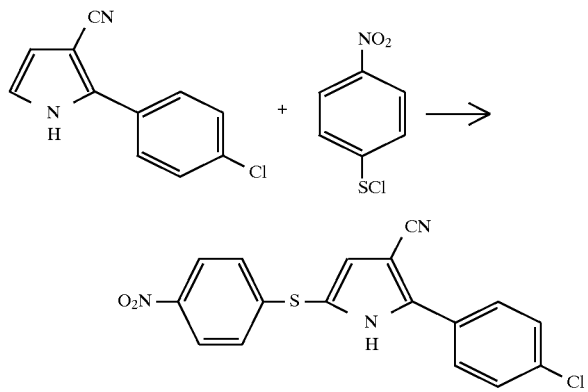

A mixture of 2-(p-chlorophenyl)pyrrole-3-carbonitrile (3.01 g, 1.5 mmol) in methylene chloride is cooled to 0 °C., treated dropwise over 30 minutes with a solution of p-nitrophenylsulfenyl chloride (2.98 g, 1.57 mmol) in methylene chloride, stirred at room temperature for 90 minutes and concentrated in vacuo to obtain a residue. A solution of the residue in ethyl acetate is washed sequentially with water and brine, dried over anhydrous sodium sulfate and concentrated in vacuo to obtain a solid. The solid is recrystallized from methanol to give the title product as a yellow solid (4.11 g, mp >230° C.).

Using essentially the same procedure, the following compounds are obtained:

| L | M | mp °C. |
|---|---|---|
| H | Cl | 190–193 |
| H | H | 165–168 |
| Cl | Cl | 209–211 |
| Cl | F | 161–163 |

EXAMPLE 8

Preparation of 2-(p-Chlorophenyl)-5-[(p-chlorophenyl)thio]-3-nitropyrrole

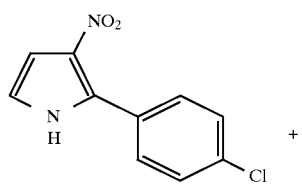

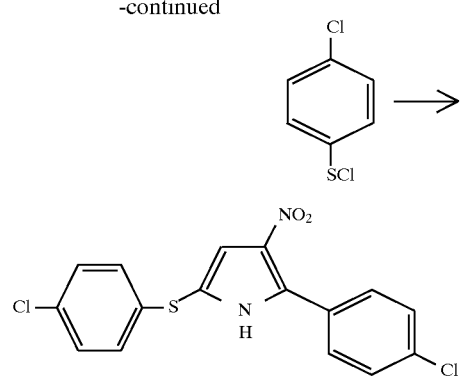

A solution of 2-(p-chlorophenyl)-3-nitropyrrole (4.88 g, 21.9 mmol) in methylene chloride is cooled to 0° C., treated dropwise over 30 minutes with a solution of p-chlorophenylsulfenyl chloride (4.32 g, 24 mmol) in methylene chloride, stirred at 0° C. for 3 hours, stirred overnight at room temperature, diluted with methylene chloride, washed sequentially with water, saturated sodium bicarbonate solution and brine, dried over anhydrous magnesium sulfate and concentrated in vacuo to obtain a dark residue. Flash column chromatography of the residue using silica gel and a 1:5 ethyl acetate/hexanes solution gives the title product as a yellow solid (2.38 g, mp 195°–197° C.).

Using essentially the same procedure, but substituting 3,4-dichlorophenylsulfenyl chloride for p-chlorophenylsulfenyl chloride, 2-(p-chlorophenyl)-5-[(3,4-dichlorophenyl)thio]-3-nitropyrrole is obtained as a yellow solid.

EXAMPLE 9

Preparation of 2-(p-Chlorophenyl)-5-(phenylsulfinyl)pyrrole-3-carbonitrile

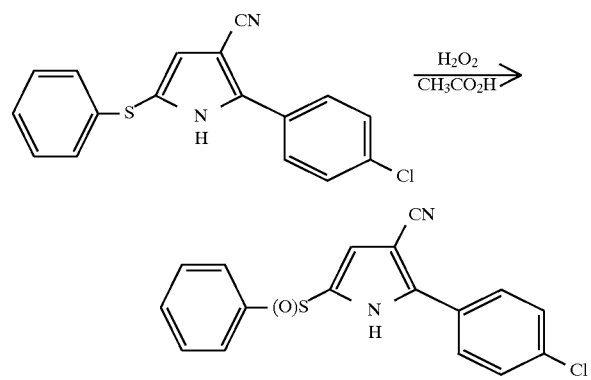

A mixture of 2-(p-chlorophenyl)-5-(phenylthio)pyrrole-3-carbonitrile (916 mg, 2.95 mmol) and 30% hydrogen peroxide solution (105.3 mg, 3.09 mmol) in acetic acid is stirred at room temperature for 3 days, diluted with water and filtered to obtain a solid. The solid is recrystallized from methanol to give the title product as a grey solid (510 mg, mp 169°–170° C.).

Using essentially the same procedure, the following compounds are obtained:

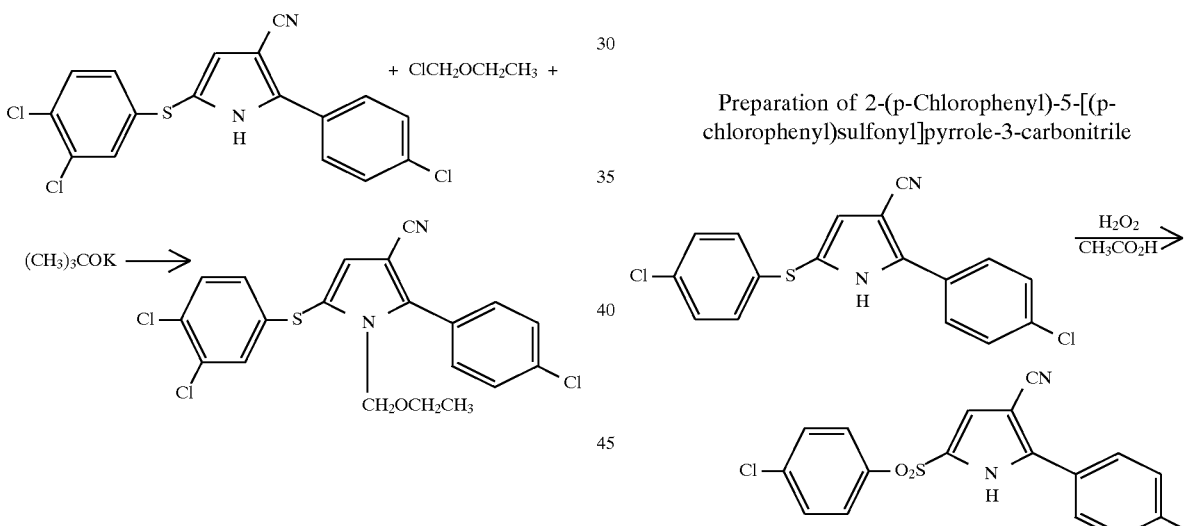

| L | M | W | R | State/mp °C. |
|---|---|---|---|---|
| H | H | NO₂ | H | 187–190 |
| Cl | Cl | CN | CH₂OC₂H₅ | 90–92 |
| Cl | F | CN | CH₂OC₂H₅ | syrup |

EXAMPLE 10

Preparation of 2-(p-chlorophenyl)-5-[(3,4-dichlorophenyl)thio]-1-(ethoxymethyl)pyrrole-3-carbonitrile A mixture of 2-(p-chlorophenyl)-5-[(3,4-dichlorophenyl) thio]pyrrole-3-carbonitrile (820 mg, 2.16 mmol) and potassium tert-butoxide (266 mg, 2.37 mmol) in tetrahydrofuran is stirred at room temperature for 30 minutes, treated with chloromethyl ethyl ether (225 mg, 2.37 mmol), stirred at room temperature for 4 hours, and diluted with water and ethyl acetate. The phases are separated and the aqueous phase is extracted with ethyl acetate. The organic phase and extracts are combined, washed with water, dried over anhydrous sodium sulfate and concentrated in vacuo to obtain a syrup. The syrup is crystallized from an ethyl acetate/hexanes solution to give the title product as a solid (780 mg, mp 95°–97° C.).

Using essentially the same procedure, the following compounds are obtained:

| W | Y | L | M | n | State/mp °C. |
|---|---|---|---|---|---|
| CN | H | H | Cl | 0 | 124–125 |
| CN | Br | H | Cl | 0 | 117.5–119.5 |
| CN | H | H | Cl | 2 | 107–109.5 |
| CN | H | H | NO₂ | 0 | 122–124 |
| CN | H | H | NO₂ | 2 | 187–190 |
| CN | Br | H | NO₂ | 0 | 142–145 |
| CN | H | H | H | 0 | syrup |
| CN | H | Cl | Cl | 2 | 131–133 |
| CN | H | Cl | F | 0 | 86–88.5 |
| CN | H | Cl | F | 2 | 128–130 |
| CN | Br | Cl | F | 2 | 156–159 |
| NO₂ | H | H | Cl | 2 | |

EXAMPLE 11

Preparation of 2-(p-Chlorophenyl)-5-[(p-chlorophenyl)sulfonyl]pyrrole-3-carbonitrile A mixture of 2-(p-chlorophenyl)-5-((p-chlorophenyl)thio] pyrrole-3-carbonitrile (1.035 g, 3 mmol) and 30% hydrogen peroxide solution (0.102 g, 9 mmol) in acetic acid is stirred at room temperature overnight, stirred at 55° C. for 5 hours and poured into an ice-water mixture. The resultant aqueous mixture is filtered to obtain a solid which is washed with water and dried overnight in a vacuum oven at 60° C. to give the title product as a colorless solid (1.03 g, mp 159°–160° C.).

Using essentially the same procedure, the following compounds are obtained:

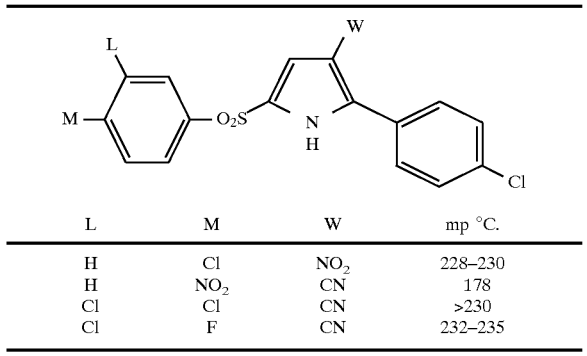

| L  | M   | W   | mp °C.  |
|----|-----|-----|---------|
| H  | Cl  | NO₂ | 228–230 |
| H  | NO₂ | CN  | 178     |
| Cl | Cl  | CN  | >230    |
| Cl | F   | CN  | 232–235 |

EXAMPLE 12

Preparation of 4-Bromo-2-(p-chlorophenyl)-[5-(p-chlorophenyl)thio]pyrrole-3-carbonitrile

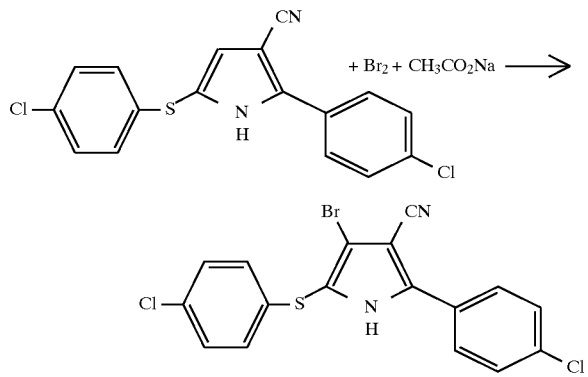

A mixture of 2-(p-chlorophenyl)-5-[(p-chlorophenyl)thio]pyrrole-3-carbonitrile (0.831 g, 2.4 mmol), bromine (0.423 g, 2.7 mmol) and sodium acetate (0.217 g, 2.7 mmol) in acetic acid is stirred at room temperature for 1 hour and poured into water. The resultant aqueous mixture is filtered to obtain a solid which is washed with water and recrystallized from 2-propanol to give the title product as colorless crystals (0.51 g, mp >230° C.).

Using essentially the same procedure, the following compounds are obtained:

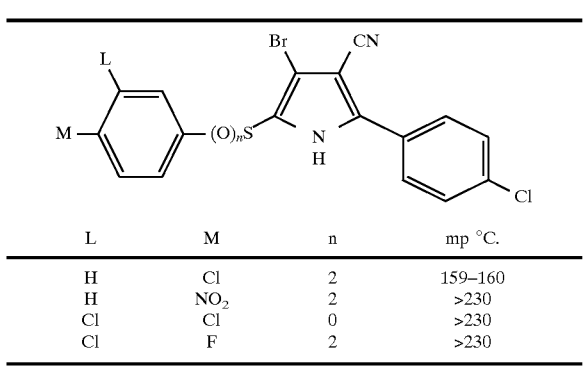

| L  | M   | n | mp °C.  |
|----|-----|---|---------|
| H  | Cl  | 2 | 159–160 |
| H  | NO₂ | 2 | >230    |
| Cl | Cl  | 0 | >230    |
| Cl | F   | 2 | >230    |

EXAMPLE 13

Preparation of 4-Bromo-2-(p-chlorophenyl)-5-[(3,4-dichlorophenyl)thio]-1-(ethoxymethyl)pyrrole-3-carbonitrile

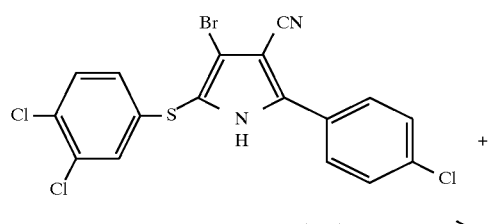

$ClCH_2OCH_2CH_3$ + $(CH_3)_3COK$ ⟶

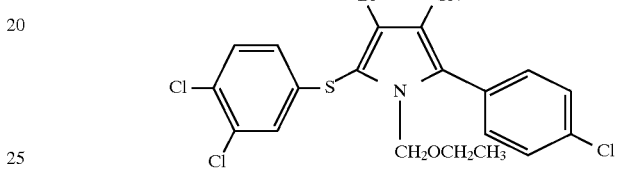

A solution of 4-bromo-2-(p-chlorophenyl)-5-[(3,4-dichlorophenyl)thio]pyrrole-3-carbonitrile (0.644 g, 1.40 mmol) and potassium tert-butoxide (0.173 g, 1.54 mmol) in tetrahydrofuran is stirred at room temperature for 30 minutes, treated with chloromethyl ethyl ether (0.16 mL, 1.54 mmol), stirred overnight at room temperature, diluted with ethyl acetate, washed with water, dried over anhydrous sodium sulfate and concentrated in vacuo to obtain a solid. The solid is recrystallized from an ethyl acetate/hexanes solution to give the title product as a white solid (0.554 g, mp 105°–107° C.).

EXAMPLE 14

Preparation of 2-(p-chlorophenyl)-4-[(3,4-dichlorophenyl)thio]-5-(trifluoromethyl)pyrrole-3-carbonitrile

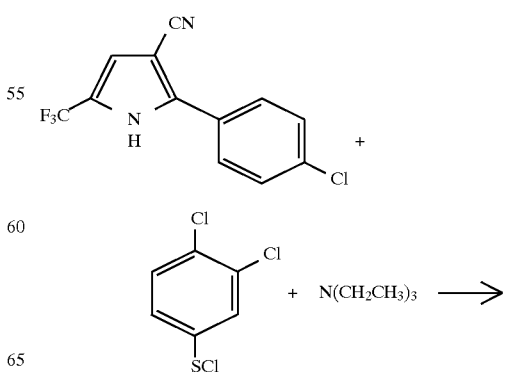

-continued

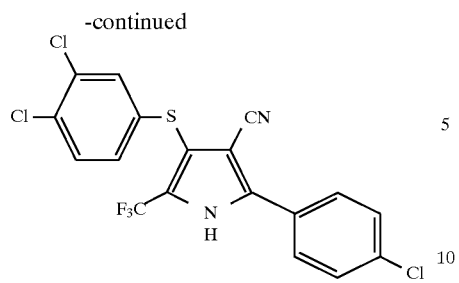

3,4-Dichlorophenylsulfenyl chloride (1.6 g, 7.49 mmol) is added to a solution of 2-(p-chlorophenyl)-5-trifluoromethylpyrrole-3-carbonitrile (2.02 g, 7.48 mmol) and triethylamine (1.67 g, 16.5 mmol) in methylene chloride. The reaction mixture is stirred at room temperature for 24 hours and concentrated in vacuo to obtain a residue. The residue is slurried in ethyl acetate and the resultant mixture is filtered to remove solids. The filtrate is diluted with hexanes to precipitate a solid which is collected and dried to give the title product as a cream colored solid (mp 94°–97° C.).

Using essentially the same procedure, the following compounds are obtained:

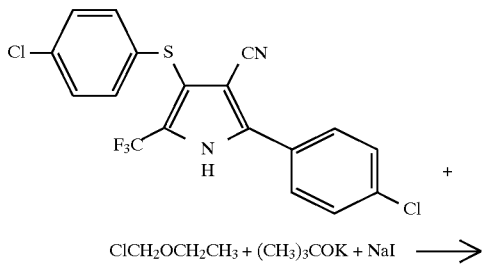

| Y | Z | mp °C. |
|---|---|---|
| H | $CF_3$ | 155–156 |
| $CF_3$ | Cl | 214–217 |

EXAMPLE 15

Preparation of 2-(p-Chlorophenyl)-4-[(p-chlorophenyl)thio]-1-(ethoxymethyl)-5-(trifluoromethyl)pyrrole-3-carbonitrile

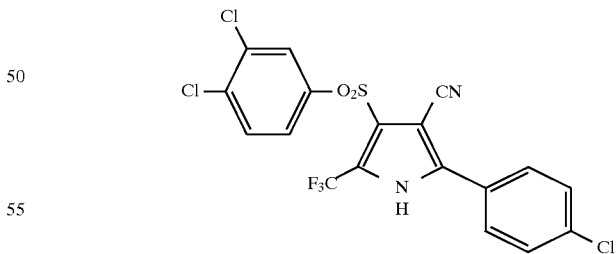

$ClCH_2OCH_2CH_3 + (CH_3)_3COK + NaI \longrightarrow$

-continued

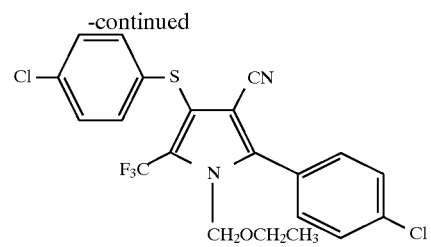

A mixture of 2-(p-chlorophenyl)-4-[(p-chlorophenyl)thio]-5-(trifluoromethyl)pyrrole-3-carbonitrile (1.7 g, 4.1 mmol), potassium tert-butoxide (0.5 g, 4.5 mmol) and sodium iodide (0.67 g, 4.5 mmol) in tetrahydrofuran is stirred at room temperature for 15 minutes, treated with chloromethyl ethyl ether (0.425 g, 4.5 mmol), stirred at room temperature for 6 hours and poured into water. The aqueous mixture is extracted with diethyl ether. The organic extract is washed sequentially with a 2 molar potassium hydroxide solution and water, dried over anhydrous sodium sulfate and concentrated in vacuo to obtain an oil. A mixture of the oil in hexanes is stored overnight at room temperature and filtered to obtain the title product as a white solid (1.25 g, mp 98°–100° C.).

Using essentially the same procedure, 2-(p-chlorophenyl)-4-[(3,4-dichlorophenyl)thio]-1-(ethoxymethyl)-5-(trifluoromethyl)pyrrole-3-carbonitrile is obtained as a white solid, mp 75°–77° C.

EXAMPLE 16

Preparation of 2-(p-Chlorophenyl)-4-[(3,4-dichlorophenyl)sulfonyl]-5-(trifluoromethyl)pyrrole-3-carbonitrile

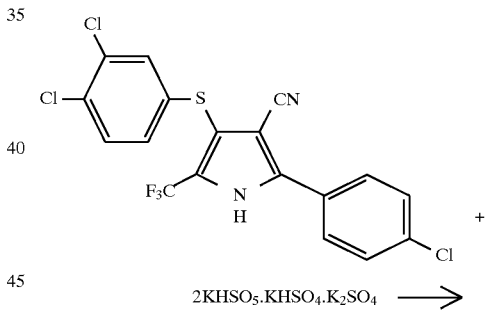

$2KHSO_5 \cdot KHSO_4 \cdot K_2SO_4 \longrightarrow$

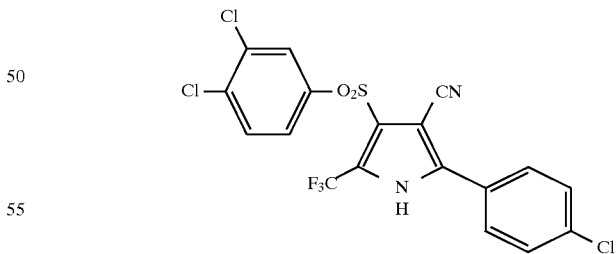

A solution of 2-(p-chlorophenyl)-4-[(3,4-dichlorophenyl)thio]-5-(trifluoromethyl)pyrrole-3-carbonitrile (1.0 g, 2.2 mmol) in methanol is treated with a solution of potassium peroxymonosulfate (2.95 g) in water (7.4 mL), stirred at 25° C. for 24 hours, diluted with additional methanol, treated with a solution of potassium peroxymonosulfate (2.7 g) in water (7.6 mL), stirred at 25° C. for 24 hours, and filtered to obtain a solid which is washed with water and dried to give the title product a white solid (mp >225° C.).

EXAMPLE 17

Preparation of 4'-Chloro-3-(1,3-dioxolan-2-yl)-2-(phenylthio)propiophenone

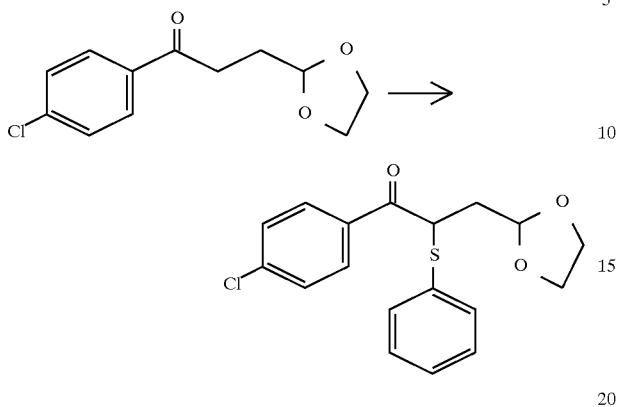

A solution of 4'-chloro-3-(1,3-dioxolan-2-yl) propiophenone (1.0 g, 4.16 mmol) in tetrahydrofuran is added dropwise to a solution of lithium diisopropylamide (3 mL of a 1.5 molar solution in tetrahydrofuran, 4.6 mmol) in tetrahydrofuran at −78° C. The reaction mixture is stirred at −78° C. for 15 minutes, treated with a solution of phenyl disulfide (2.0 g, 9.2 mmol) in tetrahydrofuran, stirred at room temperature overnight, diluted with diethyl ether, washed sequentially with 1N hydrochloric acid and brine, dried over anhydrous magnesium sulfate and concentrated in vacuo to obtain a residue. Flash column chromatography of the residue using silica gel and a 1:1 ethyl acetate/hexanes solution gives the title product as a white solid (1.0 g, mp 74°–75° C.).

EXAMPLE 18

Preparation of 2-(p-Chlorophenyl)-3-(Phenylthio) pyrrole

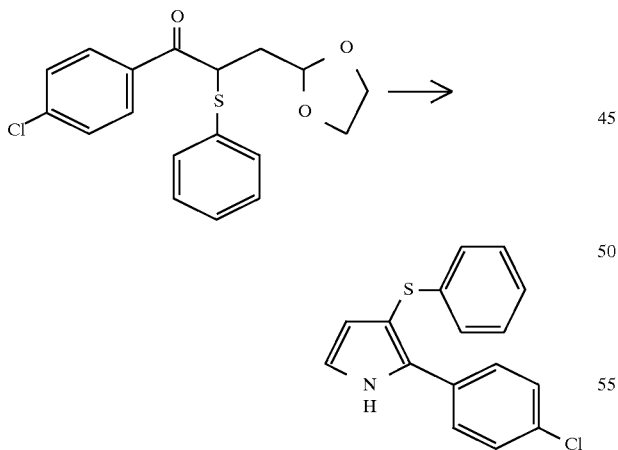

A solution of 4'-chloro-3-(1,3-dioxolan-2-yl)-2-(phenylthio)propiophenone (0.87 g, 2.5 mmol) and 4N hydrochloric acid (15 mL) in acetone is stirred at 45° C. for 3 hours, cooled, and diluted with water and ethyl acetate. The organic phase is separated, washed with 5% sodium bicarbonate solution, dried over anhydrous sodium sulfate and concentrated in vacuo to obtain a residue. A solution of the residue in acetic acid is treated with ammonium acetate (3.0 g, 0.039 mol), stirred at 45° C. for 20 minutes, cooled to room temperature, and diluted with water and ethyl acetate. The organic phase is separated, dried over anhydrous sodium sulfate and concentrated in vacuo to obtain a dark residue. Flash column chromatography of the dark residue using silica gel and a 1:1 ethyl acetate/hexanes solution gives the title product as a dark brown syrup which is identified by NMR spectral analyses.

EXAMPLE 19

Preparation of 2-(p-Chlorophenyl)-3-(phenylsulfonyl)pyrrole

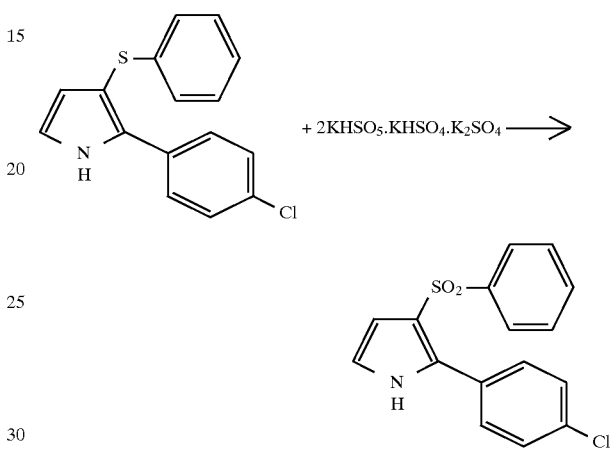

A solution of 2-(p-chlorophenyl)-3-(phenylthio)pyrrole (1.0 g, 3.5 mmol) in methanol is treated with a solution of potassium peroxymonosulfate (2.95 g) in water (7.6 mL), stirred at room temperature for 5 hours, diluted with additional methanol, treated with a solution of potassium peroxymonosulfate (2.5 g) in water (7.4 mL), stirred at room temperature overnight and filtered to obtain a solid which is washed with water and dried to give the title product as a solid (mp 158°–159° C.).

EXAMPLE 20

Preparation of 2,3-Dibromo-5-(p-chlorophenyl)-4-(phenylsulfonyl)pyrrole

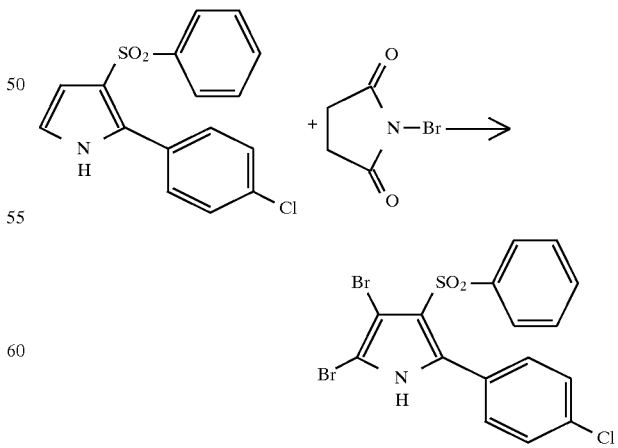

A mixture of 2-(p-chlorophenyl)-3-(phenylsulfonyl) pyrrole (0.26 g, 0.82 mmol) and N-bromosuccinimide (0.35 g, 1.97 mmol) in tetrahydrofuran is stirred at room temperature for 30 hours and concentrated in vacuo to obtain a residue. Flash column chromatography of the residue using silica gel and a 1:1 ethyl acetate/hexanes solution gives the title product as a beige solid (0.24 g, mp >200° C.)

EXAMPLE 21

Preparation of 3-chloro-5-(p-chlorophenyl)-4-(phenylsulfonyl)-2-(trifluoromethyl)pyrrole

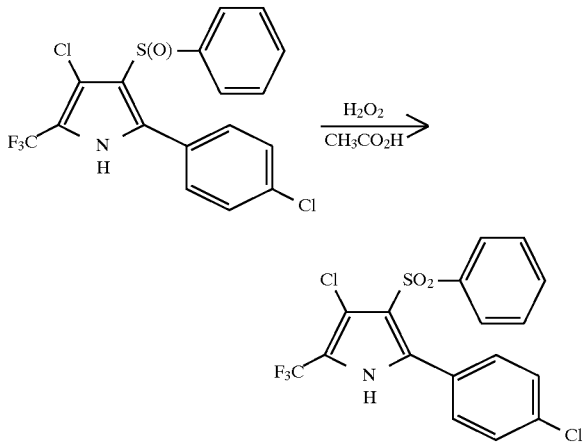

A mixture of 3-chloro-5-(p-chlorophenyl)-4-(phenylsulfinyl)-2-(trifluoromethyl)pyrrole (0.335 g, 0.83 mmol) and 30% hydrogen peroxide solution (0.28 mL, 2.49 mmol) in acetic acid is stirred at 50° C. for 7 hours, cooled and poured into an ice-water mixture. The resultant aqueous mixture is filtered to obtain a solid which is washed with water and dried to give the title product as a colorless solid (mp 158°–161° C.).

Using essentially the same procedure, the following compounds are obtained:

| Compound | mp °C. |
|---|---|
| (structure with Br, SO₂, Cl, F, F₃C, N-H, Cl) | 196–198 |
| (structure with CN, O₂S, N-CH₂OCH₂CH₃, Cl) | 129–131 |

EXAMPLE 22

Insecticide Evaluations

The following tests show the efficacy of the compounds as insecticides. The evaluations are conducted with solutions of test compounds dissolved or dispersed in 50:50 acetone/water mixtures. The test compound is technical material dissolved or dispersed in said acetone/water mixtures in sufficient amounts to provide the concentrations set forth in Table I below.

All concentrations reported herein are in terms of active ingredient. All tests are conducted in a laboratory maintained at about 27° C. The rating system employed is as follows:

| Rating System | |
|---|---|
| 0 = no effect | 5 = 56–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |
| | — = no evaluation |

The test species of insects used in the present evaluations along with specific test procedures are described below.

Spodoptera eridania third instar larvae, southern armyworm

A sieva lima bean leaf expanded to 7 to 8 cm in length is dipped in the test suspension with agitation for three seconds and placed in a hood to dry. The leaf is then placed in a 100×10 mm petri dish containing a damp filter paper on the bottom and ten third instar caterpillars. The dish is maintained for five days before observations are made of mortality, reduced feeding or any interference with normal moulting.

*Heliothis virescens*, third instar tobacco budworm

Cotton cotyledons are dipped in the test formulation and allowed to dry in a hood. When dry, each is cut into quarters and ten sections placed individually in 30 mL plastic medicine cups containing a 5 to 7 mm long piece of damp dental wick. One third instar caterpillar is added to each cup and a cardboard lid placed on the cup. Treatments are maintained for three days before mortality counts and estimates of reduction in feeding damage are made.

Compounds employed in the above described insecticide evaluations are given a compound number and identified by name. Date in Table I are reported by compound number.

| COMPOUNDS EVALUATED AS INSECTICIDAL AGENTS |
|---|
| Compound Number |

| | |
|---|---|
| 1 | 2-(p-Chlorophenyl)-4-[(3,4-dichlorophenyl)thio]-5-(trifluoromethyl)pyrrole-3-carbonitrile |
| 2 | 2-(p-Chlorophenyl)-4-[(p-chlorophenyl)thio]-5-(trifluoromethyl)pyrrole-3-carbonitrile |
| 3 | 3-Bromo-4-[(3-chloro-4-fluorophenyl)sulfonyl]-5-(p-chlorophenyl)-2-(trifluoromethyl)pyrrole |
| 4 | 3-Bromo-5-(p-chlorophenyl)-4-[(p-chlorophenyl)sulfonyl]-2-(trifluoromethyl)pyrrole |
| 5 | 4-Bromo-2-(p-chlorophenyl)-5-[(p-chlorophenyl)sulfonyl]pyrrole-3-carbonitrile |
| 6 | 2-(p-Chlorophenyl)-5-[(3,4-dichlorophenyl)sulfonyl]pyrrole-3-carbonitrile |
| 7 | 2-(p-Chlorophenyl)-5-[(3,4-dichlorophenyl)sulfonyl]-1-(ethoxymethyl)pyrrole-3-carbonitrile |
| 8 | 2,3-Dibromo-5-(p-chlorophenyl)-4-(phenylsulfonyl) pyrrole |
| 9 | 4-[(p-Chlorophenyl)thio]-2-(α,α,α-trifluoro-p-tolyl)pyrrole-3-carbonitrile |
| 10 | 2-(p-Chlorophenyl)-4-[(p-chlorophenyl)thio]-1-(ethoxymethyl)-5-(trifluoromethyl)pyrrole-3-carbonitrile |
| 11 | 2-(p-Chlorophenyl)-4-[(3,4-dichlorophenyl)thio]-1-(ethoxymethyl)-5-(trifluoromethyl)-pyrrole-3-carbonitrile |
| 12 | 2-(p-Chlorophenyl)-4-[(3,4-dichlorophenyl)- |

COMPOUNDS EVALUATED AS INSECTICIDAL AGENTS

| Compound Number | |
|---|---|
| 13 | sulfonyl)-5-(trifluoromethyl)pyrrole-3-carbonitrile 2-(p-Chlorophenyl)-3-[(p-chlorophenyl)thio]-5-(trifluoromethyl)pyrrole |
| 14 | 2-(p-Chlorophenyl)-3-[(p-chlorophenyl)sulfonyl]-5-(trifluoromethyl)pyrrole |
| 15 | 2-(p-Chlorophenyl)-5-[(p-chlorophenyl)thio]-pyrrole-3-carbonitrile |
| 16 | 4-Bromo-2-(p-chlorophenyl)-[5-(p-chlorophenyl)-thio]pyrrole-3-carbonitrile |
| 17 | 4-Bromo-2-(p-chlorophenyl)-5-[(p-chlorophenyl)-[0004]thio]-1-(ethoxymethyl)pyrrole-3-carbonitrile |
| 18 | 2-(p-Chlorophenyl)-5-[(p-chlorophenyl)thio]-1-(ethoxymethyl)pyrrole-3-carbonitrile |
| 19 | 2-(p-Chlorophenyl)-5-[(p-chlorophenyl)sulfonyl]-1-(ethoxymethyl)pyrrole-3-carbonitrile |
| 20 | 2-(p-Chlorophenyl)-5-[(p-chlorophenyl)sulfonyl]-pyrrole-3-carbonitrile |
| 21 | 3-Bromo-5-(p-chlorophenyl)-4-[(p-chlorophenyl)-sulfonyl]-1-(ethoxymethyl)-2-(trifluoromethyl)pyrrole |
| 22 | 2-(p-Chlorophenyl)-3-[(p-chlorophenyl)sulfinyl]-5-(trifluoromethyl)pyrrole |
| 23 | 2-(p-Chlorophenyl)-3-[(p-chlorophenyl)sulfinyl]-1-(ethoxymethyl)-5-(trifluoromethyl)pyrrole |
| 24 | 3-Bromo-5-(p-chlorophenyl)-4-[(p-chlorophenyl)-thio]-2-(trifluoromethyl)pyrrole |
| 25 | 2-(p-Chlorophenyl)-5-[(p-chlorophenyl)thio]-3-nitropyrrole |
| 26 | 2-(p-Chlorophenyl)-5-[(p-chlorophenyl)sulfonyl]-1-(ethoxymethyl)-3-nitropyrrole |
| 27 | 2-(p-Chlorophenyl)-5-[(p-chlorophenyl)sulfonyl]-3-nitropyrrole |
| 28 | 2-(p-Chlorophenyl)-5-[(p-chlorophenyl)sulfinyl]-3-nitropyrrole |
| 29 | 2-(p-Chlorophenyl)-5-[(p-nitrophenyl)thio]-pyrrole-3-carbonitrile |
| 30 | 2-(p-Chlorophenyl)-1-(ethoxymethyl)-5-[(p-nitrophenyl)thio]pyrrole-3-carbonitrile |
| 31 | 2-(p-Chlorophenyl)-5-[(p-nitrophenyl)sulfonyl]-pyrrole-3-carbonitrile |
| 32 | 2-(p-Chlorophenyl)-1-(ethoxymethyl)-5-[(p-nitrophenyl)sulfonyl]pyrrole-3-carbonitrile |
| 33 | 4-Bromo-2-(p-chlorophenyl)-5-[(p-nitrophenyl)-sulfonyl]pyrrole-3-carbonitrile |
| 34 | 2-(p-Chlorophenyl)-5-(phenylthio)pyrrole-3-carbonitrile |
| 35 | 2-(p-Chlorophenyl)-1-(ethoxymethyl)-5-(phenyl-thio)pyrrole-3-carbonitrile |
| 36 | 4-Bromo-2-(p-chlorophenyl)-1-(ethoxymethyl)-5-[(p-nitrophenyl)thio]pyrrole-3-carbonitrile |
| 37 | 2-(p-Chlorophenyl)-5-[(3,4-dichlorophenyl)-thio]pyrrole-3-carbonitrile |
| 38 | 2-(p-chlorophenyl)-5-(phenylsulfinyl)pyrrole-3-carbonitrile |
| 39 | 4-Bromo-2-(p-chlorophenyl)-5-[(3,4-dichlorophenyl)thio]-1-(ethoxymethyl)pyrrole-3-carbonitrile |
| 40 | 4-Bromo-2-(p-chlorophenyl)-1-(ethoxymethyl)-5-(phenylsulfonyl)pyrrole-3-carbonitrile |
| 41 | 4-Bromo-2-(p-chlorophenyl)-5-[(3,4-dichloro-phenyl)thio]pyrrole-3-carbonitrile |
| 42 | 2-(p-Chlorophenyl)-5-[(3,4-dichlorophenyl)-thio]-1-(ethoxymethyl)pyrrole-3-carbonitrile |
| 43 | 2-(p-Chlorophenyl)-5-[(3,4-dichlorophenyl)-sulfinyl]-1-(ethoxymethyl)pyrrole-3-carbonitrile |
| 44 | 5-[(3-Chloro-4-fluorophenyl)thio]-2-(p-chloro-phenyl)pyrrole-3-carbonitrile |
| 45 | 5-[(3-Chloro-4-fluorophenyl)thio]-2-(p-chloro-phenyl)-1-(ethoxymethyl)pyrrole-3-carbonitrile |
| 46 | 5-[(3-Chloro-4-fluorophenyl)sulfonyl]-2-(p-chlorophenyl)pyrrole-3-carbonitrile |
| 47 | 4-Bromo-5-[(3-chloro-4-fluorophenyl)sulfonyl]-2-(p-chlorophenyl)pyrrole-3-carbonitrile |
| 47 | 4-Bromo-5-[(3-chloro-4-fluorophenyl)sulfonyl]-2-(p-chlorophenyl)pyrrole-3-carbonitrile |
| 48 | 4-Bromo-5-[(3-chloro-4-fluorophenyl)sulfonyl]-2-(p-chlorophenyl)-1-(ethoxymethyl)pyrrole-3-carbonitrile |
| 49 | 5-[(3-Chloro-4-fluorophenyl)sulfinyl]-2-(p-chlorophenyl)-1-(ethoxymethyl)pyrrole-3-carbonitrile |
| 50 | 5-[(3-Chloro-4-fluorophenyl)sulfonyl]-2-(p-chlorophenyl)-1-(ethoxymethyl)pyrrole-3-carbonitrile |
| 51 | 2-(p-Chlorophenyl)-3-(phenylsulfinyl)-5-(tri-fluoromethyl)pyrrole |
| 52 | 2-(p-Chlorophenyl)-3-(phenylthio)-5-(tri-fluoromethyl)pyrrole |
| 53 | 3-Bromo-5-(p-chlorophenyl)-4-(phenylthio)-2-(trifluoromethyl)pyrrole |
| 54 | 3-Chloro-5-(p-chlorophenyl)-4-(phenylthio)-2-(trifluoromethyl)pyrrole |
| 55 | 2-(p-Chlorophenyl)-3-(phenylsulfonyl)-5-(tri-fluoromethyl)pyrrole |
| 56 | 3-Bromo-5-(p-chlorophenyl)-1-(ethoxymethyl)-4-(phenylthio)-2-(trifluoromethyl)pyrrole |
| 57 | 2-(p-Chlorophenyl)-1-(ethoxymethyl)-3-(phenylthio)-5-(trifluoromethyl)pyrrole |
| 58 | 2-(p-Chlorophenyl)-1-(ethoxymethyl)-3-(phenyl-sulfinyl)-5-(trifluoromethyl)pyrrole |
| 59 | 3-[(3-Chloro-4-fluorophenyl)thio]-2-(p-chloro-phenyl)-5-(trifluoromethyl)pyrrole |
| 60 | 3-Bromo-5-(p-chlorophenyl)-4-(phenylsulfonyl)-2-(trifluoromethyl)pyrrole |
| 61 | 3-Bromo-5-(p-chlorophenyl)-4-(phenylsulfinyl)-2-(trifluoromethyl)pyrrole |
| 62 | 2-(p-Chlorophenyl)-1-(ethoxymethyl)-3-(phenyl-sulfonyl)-5-(trifluoromethyl)pyrrole |
| 63 | 3-Chloro-5-(p-chlorophenyl)-4-(phenylsulfinyl)-2-(trifluoromethyl)pyrrole |
| 64 | 3-Bromo-4-[(3-chloro-4-fluorophenyl)thio]-5-(p-chlorophenyl)-2-(trifluoromethyl)pyrrole |
| 65 | 3-[(3-Chloro-4-fluorophenyl)sulfinyl]-2-(p-chlorophenyl)-5-(trifluoromethyl)pyrrole |
| 66 | 4-[(3-Chloro-4-fluorophenyl)sulfinyl]-5-(p-chlorophenyl)-2-(trifluoromethyl)pyrrole |
| 67 | 3-Bromo-4-[(3-chloro-4-fluorophenyl)thio]-5-(p-chlorophenyl)-1-(ethoxymethyl)-2-(trifluoromethyl)pyrrole |
| 68 | 3-[(3-Chloro-4-fluorophenyl)sulfinyl]-2-(p-chlorophenyl)-1-(ethoxymethyl)-5-(trifluoromethyl)pyrrole |
| 69 | 3-[(3-Chloro-4-fluorophenyl)thio]-2-(p-chloro-phenyl)-1-(ethoxymethyl)-5-(trifluoromethyl)pyrrole |
| 70 | 3-Chloro-5-(p-chlorophenyl)-4-(phenylsulfonyl)-2-(trifluoromethyl)pyrrole |
| 71 | 3-Chloro-5-(p-chlorophenyl)-1-(ethoxymethyl)-4-(phenylthio)-2-(trifluoromethyl)pyrrole |
| 72 | 3-Bromo-5-(p-chlorophenyl)-4-[(p-chlorophenyl)-sulfinyl]-2-(trifluoromethyl)pyrrole |
| 73 | 2-(p-Chlorophenyl)-3-[(p-chlorophenyl)sulfonyl]-1-(ethoxymethyl)-5-(trifluoromethyl)pyrrole |
| 74 | 3-Bromo-5-(p-chlorophenyl)-4-[(p-chlorophenyl)-sulfinyl]-1-(ethoxymethyl)-2-(trifluoromethyl)pyrrole |
| 75 | 3-Bromo-4-[(3-chloro-4-fluorophenyl)sulfinyl]-5-(p-chlorophenyl)-1-(ethoxymethyl)-2-(trifluoromethyl)pyrrole |
| 76 | 2-(p-Chlorophenyl)-3-[(p-nitrophenyl)thio]-5-(trifluoromethyl)pyrrole |
| 77 | 2-(p-Chlorophenyl)-1-(ethoxymethyl)-3-[(p-nitrophenyl)thio]-5-(trifluoromethyl)pyrrole |

Row above 49: 2-(p-chlorophenyl)-1-(ethoxymethyl)pyrrole-3-carbonitrile

TABLE I

Insecticidal Evaluations

| Compound Number | Southern Armyworm (ppm) 1000 | Southern Armyworm (ppm) 300 | Southern Armyworm (ppm) 100 | Tobacco Budworm (ppm) 300 | Tobacco Budworm (ppm) 100 |
|---|---|---|---|---|---|
| 1 | 9 | 9 | 9 | — | 9 |
| 2 | 9 | 9 | 9 | — | 9 |
| 3 | 9 | 9 | 9 | — | 9 |
| 4 | 9 | 9 | 9 | 9 | 9 |
| 5 | 9 | 9 | 9 | 9 | 9 |
| 6 | 9 | 9 | 9 | 9 | 9 |
| 7 | 9 | 9 | 9 | 9 | 9 |
| 8 | 9 | — | 0 | — | 0 |
| 9 | 9 | — | 9 | — | 8 |
| 10 | 9 | — | 9 | — | 9 |
| 11 | 9 | — | 9 | — | 7 |
| 12 | 9 | — | 5 | — | 0 |
| 13 | 9 | 9 | 3 | — | — |
| 14 | 9 | 9 | 9 | 9 | 9 |
| 15 | 9 | 9 | 9 | — | — |
| 16 | 9 | 0 | 0 | — | — |
| 17 | 9 | 9 | 9 | 8 | 8 |
| 18 | 9 | 9 | 9 | — | — |
| 19 | 9 | 9 | 9 | 9 | 9 |
| 20 | 9 | 9 | 9 | 9 | 9 |
| 21 | 9 | 9 | 9 | 9 | 9 |
| 22 | 9 | 9 | 9 | — | — |
| 23 | 9 | 9 | 9 | — | — |
| 24 | 9 | 9 | 9 | — | — |
| 25 | 9 | 9 | 9 | 8 | 8 |
| 26 | 9 | 9 | 9 | 9 | 9 |
| 27 | 9 | 9 | 9 | 9 | 9 |
| 28 | 9 | 9 | 9 | 9 | 9 |
| 29 | 2 | — | — | — | — |
| 30 | 0 | — | — | — | — |
| 31 | 5 | — | — | — | — |
| 32 | 3 | — | — | — | — |
| 33 | 8 | 6 | 5 | — | — |
| 34 | 9 | 9 | 9 | 0 | 0 |
| 35 | 9 | 9 | 9 | — | — |
| 36 | 9 | 0 | 0 | — | — |
| 37 | 9 | 9 | 9 | 9 | 9 |
| 38 | 9 | 9 | 9 | — | — |
| 39 | 9 | 9 | 3 | — | — |
| 40 | 9 | 9 | 9 | — | — |
| 41 | 9 | 9 | 9 | — | — |
| 42 | 9 | 9 | 9 | — | — |
| 43 | 9 | 9 | 9 | 9 | 9 |
| 44 | 9 | 9 | 9 | — | — |
| 45 | 9 | 9 | 9 | — | — |
| 46 | 9 | 9 | 9 | — | — |
| 47 | 9 | 9 | 9 | 9 | 9 |
| 48 | 9 | 5 | 5 | — | — |
| 49 | 9 | 9 | 9 | 9 | 9 |
| 50 | 9 | 9 | 9 | 9 | 9 |
| 51 | 7 | 0 | 0 | — | — |
| 52 | 8 | 0 | 0 | 0 | 0 |
| 53 | 9 | 8 | 0 | — | — |
| 54 | 9 | 6 | 4 | 1 | 0 |
| 55 | 9 | 8 | 8 | — | — |
| 56 | 9 | 9 | 6 | 0 | 0 |
| 57 | 3 | — | — | — | — |
| 58 | 6 | — | — | — | — |
| 59 | 4 | — | — | — | — |
| 60 | 9 | 9 | 9 | — | — |
| 61 | 9 | 9 | 9 | 9 | 3 |
| 62 | 9 | 0 | 0 | — | — |
| 63 | 9 | 9 | 9 | 8 | 4 |
| 64 | 9 | 9 | 9 | — | — |
| 65 | 8 | 2 | 2 | 3 | 0 |
| 66 | 9 | 9 | 9 | 9 | 9 |
| 67 | 9 | 9 | 9 | 9 | 9 |
| 68 | 9 | 7 | 7 | 2 | 0 |
| 69 | 9 | 7 | 5 | — | — |
| 70 | 9 | 9 | 9 | 8 | 3 |
| 71 | 9 | 6 | 4 | — | — |
| 72 | 9 | 9 | 9 | — | — |
| 73 | 9 | 9 | 9 | — | — |
| 74 | 9 | 9 | 9 | — | — |
| 75 | 9 | 9 | 9 | — | — |
| 76 | 9 | 8 | 4 | — | — |
| 77 | 6 | — | — | — | — |

What is claimed is:

1. A compound having the structural formula

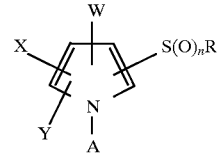

wherein

R and X are each independently phenyl optionally substituted with any combination of from one to five halogen, $NO_2$, CN, $C_1$–$C_4$alkyl, $C_1$–$C_4$haloalkyl, $C_1$–$C_4$alkoxy or $C_1$–$C_4$haloalkoxy groups;

n is an integer of 0, 1 or 2;

W is halogen, CN, $NO_2$ or $C_1$–$C_4$haloalkyl;

Y is hydrogen, halogen or $C_1$–$C_4$haloalkyl;

A is hydrogen, CN, $C(O)R_1$, $CHR_2NHC(O)R_3$, $CH_2SQ$, $CHR_4OC(O)$ $(CR_5R_6)_mQ_l$, $C_1$–$C_6$alkyl optionally substituted with
one to three halogen atoms,
one tri($C_1$–$C_4$alkyl)silyl,
one hydroxy,
one cyano,
one or two $C_1$–$C_4$alkoxy groups optionally substituted with one to three halogen atoms,
one $C_1$–$C_4$alkylthio,
one phenyl optionally substituted with one to three halogen atoms, one to three $C_1$–$C_4$alkyl groups or one to three $C_1$–$C_4$alkoxy groups,
one phenoxy group optionally substituted with one to three halogen atoms, one to three $C_1$–$C_4$alkyl groups or one to three $C_1$–$C_4$alkoxy groups,
one benzyloxy group optionally substituted on the phenyl ring with one to three halogen atoms, one to three $C_1$–$C_4$alkyl groups or one to three $C_1$–$C_4$alkoxy groups,
one $C_1$–$C_6$alkylcarbonyloxy group optionally substituted with one to three halogen atoms,
one $C_2$–$C_6$alkenylcarbonyloxy group optionally substituted with one to three halogen atoms,
one phenylcarbonyloxy group optionally substituted with one to three halogen atoms, one to three $C_1$–$C_4$alkyl groups or one to three $C_1$–$C_4$alkoxy groups,
one $C_1$–$C_6$alkoxycarbonyl group optionally substituted with one to three halogen atoms or one to three $C_1$–$C_4$alkoxy groups, or
one benzylcarbonyloxy group optionally substituted on the phenyl ring with one to three halogen atoms, one to three $C_1$–$C_4$alkyl groups or one to three $C_1$–$C_4$alkoxy groups, $C_3$–$C_6$alkenyl optionally substituted with one to three halogen atoms or one phenyl group, or $C_3$–$C_6$alkynyl optionally substituted with one to three halogen atoms or one phenyl group;

$R_1$ is $C_1$–$C_6$alkyl or $C_3$–$C_6$cycloalkyl each optionally substituted with
one to three halogen atoms,
one hydroxy,
one cyano,
one or two $C_1$–$C_4$alkoxy groups optionally substituted with one to three halogen atoms,
one $C_1$–$C_4$alkylthio,
one phenyl group optionally substituted with one to three halogen atoms, one to three $C_1$–$C_4$alkyl groups or one to three $C_1$–$C_4$alkoxy groups,
one phenoxy group optionally substituted with one to three halogen atoms, one to three $C_1$–$C_4$alkyl groups or one to three $C_1$–$C_4$alkoxy groups,
one benzyloxy group optionally substituted on the phenyl ring with one to three halogen atoms, one to three $C_1$–$C_4$alkyl groups or one to three $C_1$–$C_4$alkoxy groups,
one $C_1$–$C_6$alkylcarbonyloxy group optionally substituted with one to three halogen atoms,
one $C_2$–$C_6$alkenylcarbonyloxy group optionally substituted with one to three halogen atoms,
one phenylcarbonyloxy group optionally substituted with one to three halogen atoms, one to three $C_1$–$C_4$alkyl groups or one to three $C_1$–$C_4$alkoxy groups,
one $C_1$–$C_6$alkoxycarbonyl group optionally substituted with one to three halogen atoms or one to three $C_1$–$C_4$alkoxy groups, or
one benzyloxycarbonyl group optionally substituted on the phenyl ring with one to three halogen atoms, one to three $C_1$–$C_4$alkyl groups or one to three $C_1$–$C_4$alkoxy groups,
$C_2$–$C_6$alkenyl optionally substituted with one to three halogen atoms or one phenyl group,
$C_3$–$C_6$alkynyl optionally substituted with one to three halogen atoms or one phenyl group,
phenyl optionally substituted with one or more halogen atoms, $C_1$–$C_4$alkyl groups, $C_1$–$C_4$alkoxy groups, phenoxy groups, $C_1$–$C_4$alkylthio groups, tri($C_1$–$C_4$alkyl)silyl groups, $C_1$–$C_4$alkylsulfinyl groups, $C_1$–$C_4$alkylsulfonyl groups, CN groups, $NO_2$ groups or $CF_3$ groups,
phenoxy optionally substituted with one or more halogen atoms, $C_1$–$C_4$alkyl groups, $C_1$–$C_4$alkoxy groups, $C_1$–$C_4$alkylthio groups, tri($C_1$–$C_4$alkyl)silyl groups, $C_1$–$C_4$alkylsulfinyl groups, $C_1$–$C_4$alkylsulfonyl groups, CN groups, $NO_2$ groups or $CF_3$ groups,
1- or 2-naphthyl,
2-, 3- or 4-pyridyl optionally substituted with one to three halogen atoms,
$C_1$–$C_6$alkoxy optionally substituted with one to three halogen atoms, or
$C_2$–$C_6$alkenyloxy optionally substituted with one to three halogen atoms;

$R_2$ is hydrogen or $C_1$–$C_4$alkyl;

$R_3$ is $C_1$–$C_6$alkyl optionally substituted with one to three halogen atoms,
phenyl optionally substituted with one to three halogen atoms, CN groups, $NO_2$ groups, $C_1$–$C_4$alkyl groups, $C_1$–$C_4$alkoxy groups or $CF_3$ groups,
2- or 3-thienyl, or
2- or 3-furyl;

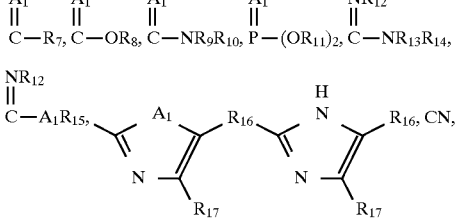

$C_1$–$C_6$alkyl optionally substituted with one or more halogen atoms, CN groups or phenyl groups, or
phenyl optionally substituted with one or more halogen atoms, $C_1$–$C_4$alkyl groups, $C_1$–$C_4$alkoxy groups, CN groups, $NO_2$ groups, $CF_3$ groups or $NR_{18}R_{19}$ groups;

$A_1$ is O or S;

$R_7$ is $C_1$–$C_6$alkyl or phenyl;

$R_8$ is $C_1$–$C_6$alkyl;

$R_9$ and $R_{10}$ are each independently hydrogen, $C_1$–$C_6$alkyl or may be taken together with the atom to which they are attached to form a 5- to 7-membered heterocyclic ring;

$R_{11}$ is $C_1$–$C_4$alkyl;

$R_{12}$ is hydrogen, $C_1$–$C_4$alkyl or may be taken together with either $R_{13}$ or $R_{15}$ and the atoms to which they are attracted to form a 5- to 7-membered heterocyclic ring optionally substituted with one or two $C_1$–$C_4$alkyl groups;

$R_{13}$ and $R_{14}$ are each independently hydrogen or $C_1$–$C_4$alkyl;

$R_{15}$ is $C_1$–$C_4$alkyl or when taken together with $R_{12}$ and the atoms to which they are attached may form a 5- to 7-membered heterocyclic ring optionally substituted with one or two $C_1$–$C_4$alkyl groups;

$R_{16}$ and $R_{17}$ are each independently hydrogen or $C_1$–$C_4$alkyl or when taken together may form a ring wherein $R_{16}R_{17}$ is represented by —CH=CH—CH=CH—;

$R_{18}$ and $R_{19}$ are each independently hydrogen or $C_1$–$C_4$alkyl;

$R_4$ is hydrogen or $C_1$–$C_4$alkyl;

$R_5$ and $R_6$ are each independently hydrogen,
$C_1$–$C_6$alkyl optionally substituted with one or more halogen atoms,
$C_1$–$C_6$alkoxy optionally substituted with one or more halogen atoms,
$C_1$–$C_6$alkylthio optionally substituted with one or more halogen atoms, or
phenyl optionally substituted with one or more halogen atoms,
$NO_2$ groups;
CN groups,
$C_1$–$C_4$alkyl groups optionally substituted with one or more halogen atoms, or
$C_1$–$C_4$alkoxy groups optionally substituted with one or more halogen atoms, or
when $R_5$ and $R_6$ are taken together with the atom to which they are attached may form a $C_3$–$C_6$cycloalkyl group optionally substituted with one to three $C_1$–$C_4$alkyl groups, $C_2$–$C_6$alkenyl groups or phenyl groups, or $R_5$ or $R_6$ may be taken together with $R_{20}$ and the atoms to which they are attached to form a 4- to 7-membered heterocyclic ring;

m is an integer of 0, 1, 2, 3 or 4;

$Q_1$ is $A_2R_{20}$,

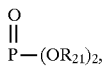

$NR_{22}R_{23}$, $CR_{24}R_{25}C(O)R_{26}$, or
$C_3$–$C_6$cycloalkyl optionally substituted with one or more $C_1$–$C_6$alkyl groups, $C_2$–$C_6$alkenyl groups, or phenyl groups optionally substituted with
    one or more halogen atoms,
    $NO_2$ groups,
    CN groups,
    $C_1$–$C_4$alkyl groups optionally substituted with one or more halogen atoms, or
    $C_1$–$C_4$alkoxy groups optionally substituted with one or more halogen atoms;

$A_2$ is O or $S(O)_p$;
p is an integer of 0, 1 or 2;
$R_{20}$ is hydrogen,
  $C_1$–$C_6$alkyl,
  $C_2$–$C_6$alkenyl,
  $C_2$–$C_6$alkynyl,
  phenyl optionally substituted with one or more
    halogen atoms,
    $NO_2$ groups,
    CN groups,
    $C_1$–$C_4$alkyl groups optionally substituted with one or more halogen atoms,
    $C_1$–$C_4$alkoxy groups optionally substituted with one or more halogen atoms,
  $C(O)R_{27}$ provided p is 0,
  $C(O)R_{28}$ provided p is 0,
  $(CH_2CH_2O)_qR_{27}$, or

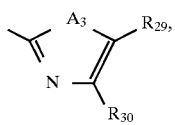

or
$R_{20}$ may be taken together with either $R_5$ or $R_6$ and the atoms to which they are attached to form a 4- to 7-membered heterocyclic ring;
$A_3$ is O or S;
$R_{27}$ is $C_1$–$C_6$alkyl,
  $C_2$–$C_6$alkenyl,
  $C_2$–$C_6$alkynyl, or
  phenyl optionally substituted with one or more
    halogen atoms,
    $NO_2$ groups,
    CN groups,
    $C_1$–$C_4$alkyl groups optionally substituted with one or more halogen atoms, or
    $C_1$–$C_4$alkoxy groups optionally substituted with one or more halogen atoms;
q is an integer of 1, 2 or 3;
$R_{28}$ is $OR_{31}$ or $NR_{32}R_{33}$;
$R_{31}$ is $C_1$–$C_6$alkyl or
  phenyl optionally substituted with one or more
    halogen atoms,
    $NO_2$ groups,
    CN groups,
    $C_1$–$C_4$alkyl groups optionally substituted with one or more halogen atoms, or
    $C_1$–$C_4$alkoxy groups optionally substituted with one or more halogen atoms;
$R_{32}$ and $R_{33}$ are each independently hydrogen or $C_1$–$C_4$alkyl;
$R_{29}$ and $R_{30}$ are each independently hydrogen or $C_1$–$C_4$alkyl, or when taken together may form a ring wherein $R_{29}R_{30}$ is represented by —CH=CH—CH=CH—;
$R_{21}$ is $C_1$–$C_4$alkyl;
$R_{22}$ is hydrogen,
  $C_1$–$C_6$alkyl,
  $C_2$–$C_6$alkenyl,
  $C_2$–$C_6$alkynyl, or
  phenyl optionally substituted with one or more
    halogen atoms,
    $NO_2$ groups,
    CN groups,
    $C_1$–$C_4$alkyl groups optionally substituted with one or more halogen atoms, or
    $C_1$–$C_4$alkoxy groups optionally substituted with one or more halogen atoms, or
$R_{22}$ may be taken together with either $R_5$ or $R_6$ and the atoms to which they are attached to form a 4- to 7-membered heterocyclic ring;
$P_{23}$ is hydrogen,
  $C_1$–$C_6$alkyl,
  $C_2$–$C_6$alkenyl,
  $C_2$–$C_6$alkynyl,
  phenyl optionally substituted with one or more
    halogen atoms,
    $NO_2$ groups,
    CN groups,
    $C_1$–$C_4$alkyl groups optionally substituted with one or more halogen atoms, or
    $C_1$–$C_4$alkoxy groups optionally substituted with one or more halogen atoms,
  $C(A_4)R_{34}$,
  CN,
  $SO_2R_{35}$, or
  $C(O)CHR_{36}NHR_{37}$;
$A_4$ is O or S;
$R_{34}$ is $OR_{38}$, $CO_2R_{38}$, $NR_{39}R_{40}$,
  $C_1$–$C_6$alkyl optionally substituted with one to three halogen atoms,
  $C_2$–$C_6$alkenyl,
  $C_2$–$C_6$alkynyl, or
  phenyl optionally substituted with one or more
    halogen atoms,
    $NO_2$ groups,
    CN groups,
    $C_1$–$C_4$alkyl groups optionally substituted with one or more halogen atoms, or
    $C_1$–$C_4$alkoxy groups optionally substituted with one or more halogen atoms;
$R_{38}$ is $C_1$–$C_6$alkyl optionally substituted with one phenyl group, or
  phenyl optionally substituted with one or more
    halogen atoms,
    $NO_2$ groups,
    CN groups,
    $C_1$–$C_4$alkyl groups optionally substituted with one or more halogen atoms, or
    $C_1$–$C_4$alkoxy groups optionally substituted with one or more halogen atoms;
$R_{39}$ and $R_{40}$ are each independently hydrogen or $C_1$–$C_4$alkyl;

$R_{35}$ is $NR_{41}R_{42}$,
  $C_1$–$C_6$alkyl,
  $C_2$–$C_6$alkenyl,
  $C_2$–$C_6$alkynyl, or
  phenyl optionally substituted with one or more
    halogen atoms,
    $NO_2$ groups,
    CN groups,
    $C_1$–$C_4$alkyl groups optionally substituted with one or more halogen atoms, or
    $C_1$–$C_4$alkoxy groups optionally substituted with one or more halogen atoms;

$R_{41}$ and $R_{42}$ are each independently hydrogen or $C_1$–$C_4$alkyl;

$R_{36}$ is hydrogen,
  $C_1$–$C_4$alkyl optionally substituted with
    one hydroxy group,
    one $SR_{43}$ group,
    one $C(O)NH_2$ group,
    one $NH_2$ group,
    one $NHC(=NH)NH_2$ group,
    one $CO_2H$ group,
    one phenyl group optionally substituted with one hydroxy group,
    one 3-indolyl group or
    one 4-imidazolyl group;

$R_{43}$ is hydrogen of $C_1$–$C_4$alkyl;

$R_{37}$ is $C(A_4)R_{44}$;

$R_{44}$ is $C_1$–$C_6$alkyl optionally substituted with one or more halogen atoms,
  $C_2$–$C_6$alkoxyalkyl,
  $C_1$–$C_6$alkylthio,
  phenyl optionally substituted with one or more
    halogen atoms,
    $NO_2$ groups,
    CN groups,
    $C_1$–$C_4$alkyl groups optionally substitutes with one or more halogen atoms, or
    $C_1$–$C_4$alkoxy groups optionally substituted with one or more halogen atoms,
  $OR_{38}$,
  $CO_2R_{38}$ or
  $NR_{39}R_{40}$;

$R_{24}$ and $R_{25}$ are each independently hydrogen,
  $C_1$–$C_6$alkyl optionally substituted with one or more halogen atoms,
  $C_1$–$C_6$alkoxy optionally substituted with one or more halogen atoms,
  $C_1$–$C_6$alkylthio optionally substituted with one or more halogen atoms,
  phenyl optionally substituted with one or more
    halogen atoms,
    CN groups,
    $NO_2$ groups,
    $C_1$–$C_4$alkyl groups optionally substituted with one or more halogen atoms, or
    $C_1$–$C_4$alkoxy groups optionally substituted with one or more halogen atoms, or
when $R_{24}$ and $R_{25}$ are taken together with the atom to which they are attached may form a $C_3$–$C_6$cycloalkyl group optionally substituted with one to three $C_1$–$C_4$alkyl groups, $C_2$–$C_6$alkenyl groups or phenyl groups;

$R_{26}$ is $OR_{45}$, $NR_{41}R_{42}$, $C_1$–$C_4$alkyl or phenyl optionally substituted with one or more halogen atoms,
  CN groups,
  $NO_2$ groups,
  $C_1$–$C_4$alkyl groups optionally substituted with one or more halogen atoms, or
  $C_1$–$C_4$alkoxy groups optionally substituted with one or more halogen atoms; and $R_{45}$ is $C_1$–$C_4$alkyl or
  phenyl optionally substituted with one or more
    halogen atoms,
    CN groups,
    $NO_2$ groups,
    $C_1$–$C_4$alkyl groups optionally substituted with one or more halogen atoms, or
    $C_1$–$C_4$alkoxy groups optionally substituted with one or more halogen atoms.

2. The compound according to claim 1 wherein

R and X are each independently phenyl optionally substituted with any combination of from one to three halogen, $NO_2$, CN, $C_1$–$C_4$alkyl, $C_1$–$C_4$haloalkyl, $C_1$–$C_4$alkoxy or $C_1$–$C_4$haloalkoxy groups;

n is an integer of 0, 1 or 2;

W is Cl, Br, CN, $NO_2$ or $C_1$–$C_4$haloalkyl;

Y is hydrogen, Cl, Br or $C_1$–$C_4$haloalkyl;

A is hydrogen, CN, $C(O)R_1$ or
  $C_1$–$C_4$alkyl optionally substituted with
    one to three halogen atoms,
    one cyano,
    one $C_1$–$C_4$alkoxy group,
    one $C_1$–$C_6$alkylcarbonyloxy group,
    one phenylcarbonyloxy group optionally substituted with one to three halogen atoms or one $C_1$–$C_4$alkyl group, or
    one benzylcarbonyloxy group; and $R_1$ is phenyl optionally substituted with one to three halogen atoms, one or two $C_1$–$C_4$alkyl groups, one or two $C_1$–$C_4$alkoxy groups, one CN group, one $NO_2$ group or one $CF_3$ group.

3. The compound according to claim 2 having the structural formula

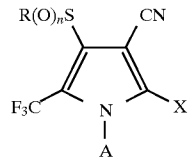

wherein

R and X are each independently phenyl optionally substituted with any combination of from one to three halogen, $NO_2$ or $CF_3$ groups;

n is an integer of 0, 1 or 2; and

A is hydrogen or $C_1$–$C_4$alkyl substituted with one $C_1$–$C_4$alkoxy group.

4. The compound according to claim 2 having the structural formula

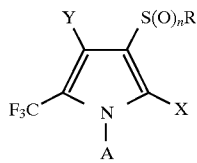

wherein

R and X are each independently phenyl optionally substituted with any combination of from one to three halogen, $NO_2$ or $CF_3$ groups;

n is an integer of 0, 1 or 2;

Y is Cl or Br; and

A is hydrogen or $C_1$–$C_4$alkyl substituted with one $C_1$–$C_4$alkoxy group.

5. The compound according to claim 2 having the structural formula

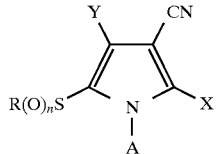

wherein

R and X are each independently phenyl optionally substituted with any combination of from one to three halogen, $NO_2$ or $CF_3$ groups;

n is an integer of 0, 1 or 2;

Y is hydrogen, Cl or Br; and

A is hydrogen or $C_1$–$C_4$alkyl substituted with one $C_1$–$C_4$alkoxy group.

6. The compound according to claim 2 selected from the group consisting of 2-(p-chlorophenyl)-4-[(3,4-dichlorophenyl)thio]-5-(trifluoromethyl)pyrrole-3-carbonitrile;

2-(p-chlorophenyl)-4-[(p-chlorophenyl)thio]-5-(trifluoromethyl)pyrrole-3-carbonitrile;

3-bromo-4-[(3-chloro-4-fluorophenyl)sulfonyl]-5-(p-chlorophenyl)-2-(trifluoromethyl)pyrrole;

3-bromo-5-(p-chlorophenyl)-4-[(p-chlorophenyl)sulfonyl]-2-(trifluoromethyl)pyrrole;

4-bromo-2-(p-chlorophenyl)-5-[(p-chlorophenyl)sulfonyl]pyrrole-3-carbonitrile;

2-(p-chlorophenyl)-5-[(3,4-dichlorophenyl)sulfonyl]pyrrole-3-carbonitrile; and 2-(p-chlorophenyl)-5-[(3,4-dichlorophenyl)sulfonyl]-1-(ethoxymethyl)pyrrole-3-carbonitrile.

7. A method for controlling insects which comprises contacting said insects, their breeding grounds, food supply or habitat with an insecticidally effective amount of a compound having the structural formula

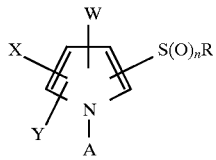

wherein A, R, W, X, Y and n are as described in claim 1.

8. The method according to claim 7 wherein A, R, W, X, Y and n are as described in claim 2.

9. The method according to claim 8 wherein the compound has the structural formula

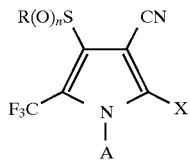

wherein

R and X are each independently phenyl optionally substituted with any combination of from one to three halogen, $NO_2$ or $CF_3$ groups;

n is an integer of 0, 1 or 2; and

A is hydrogen or $C_1$–$C_4$alkyl substituted with one $C_1$–$C_4$alkoxy group.

10. The method according to claim 8 wherein the compound has the structural formula

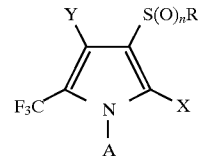

wherein

R and X are each independently phenyl optionally substituted with any combination of from one to three halogen, $NO_2$ or $CF_3$ groups;

n is an integer of 0, 1 or 2;

Y is Cl or Br; and

A is hydrogen or $C_1$–$C_4$alkyl substituted with one $C_1$–$C_4$alkoxy group.

11. The method according to claim 8 wherein the compound has the structural formula

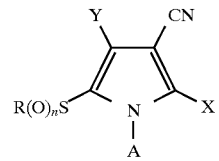

wherein

R and X are each independently phenyl optionally substituted with any combination of from one to three halogen, $NO_2$ or $CF_3$ groups;

n is an integer of 0, 1 or 2;

Y is hydrogen, Cl or Br; and

A is hydrogen or $C_1$–$C_4$alkyl substituted with one $C_1$–$C_4$alkoxy group.

12. The method according to claim 8 wherein the compound is selected from the group consisting of 2-(p-chlorophenyl)-4-[(3,4-dichlorophenyl)thio]-5-(trifluoromethyl)pyrrole-3-carbonitrile;

2-(p-chlorophenyl)-4-[(p-chlorophenyl)thio]-5-(trifluoromethyl)pyrrole-3-carbonitrile;

3-bromo-4-[(3-chloro-4-fluorophenyl)sulfonyl]-5-(p-chlorophenyl)-2-(trifluoromethyl)pyrrole;

3-bromo-5-(p-chlorophenyl)-4-[(p-chlorophenyl)sulfonyl]-2-(trifluoromethyl)pyrrole;

4-bromo-2-(p-chlorophenyl)-5-[(p-chlorophenyl)sulfonyl]pyrrole-3-carbonitrile;

2-(p-chlorophenyl)-5-[(3,4-dichlorophenyl)sulfonyl]pyrrole-3-carbonitrile; and 2-(p-chlorophenyl)-5-[(3,4-dichlorophenyl)sulfonyl]-1-(ethoxymethyl)pyrrole-3-carbonitrile.

13. A method for protecting growing plants from attack by insects which comprises applying to the foliage of said plants or to the soil or water in which they are growing an insecticidally effective amount of a compound having the structural formula

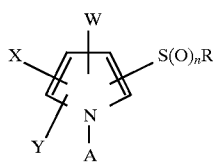

wherein A, R, W, X, Y and n are as described in claim 1.

14. The method according to claim 13 wherein A, R, W, X, Y and n are as described in claim 2.

15. The method according to claim 14 wherein the compound has the structural formula

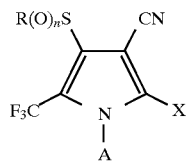

wherein

R and X are each independently phenyl optionally substituted with any combination of from one to three halogen, $NO_2$ or $CF_3$ groups;

n is an integer of 0, 1 or 2; and

A is hydrogen or $C_1$–$C_4$alkyl substituted with one $C_1$–$C_4$alkoxy group.

16. The method according to claim 14 wherein the compound has the structural formula

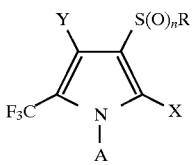

wherein

R and X are each independently phenyl optionally substituted with any combination of from one to three halogen, $NO_2$ or $CF_3$ groups;

n is an integer of 0, 1 or 2;

Y is Cl or Br; and

A is hydrogen or $C_1$–$C_4$alkyl substituted with one $C_1$–$C_4$alkoxy group.

17. The method according to claim 14 wherein the compound has the structural formula

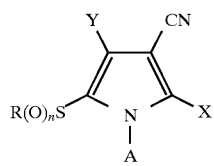

wherein

R and X are each independently phenyl optionally substituted with any combination of from one to three halogen, $NO_2$ or $CF_3$ groups;

n is an integer of 0, 1 or 2;

is hydrogen, Cl or Br; and

A is hydrogen or $C_1$–$C_4$alkyl substituted with one $C_1$–$C_4$alkoxy group.

18. The method according to claim 14 wherein the compound is selected from the group consisting of
2-(p-chlorophenyl)-4-[(3,4-dichlorophenyl)thio]-5-(trifluoromethyl)pyrrole-3-carbonitrile;
2-(p-chlorophenyl)-4-[(p-chlorophenyl)thio]-5-(trifluoromethyl)pyrrole-3-carbonitrile;
3-bromo-4-[(3-chloro-4-fluorophenyl)sulfonyl]-5-(p-chlorophenyl)-2-(trifluoromethyl)pyrrole;
3-bromo-5-(p-chlorophenyl)-4-[(p-chlorophenyl)sulfonyl]-2-(trifluoromethyl)pyrrole;
4-bromo-2-(p-chlorophenyl)-5-[(p-chlorophenyl)sulfonyl]pyrrole-3-carbonitrile;
2-(p-chlorophenyl)-5-[(3,4-dichlorophenyl)sulfonyl]pyrrole-3-carbonitrile; and
2-(p-chlorophenyl)-5-[(3,4-dichlorophenyl)sulfonyl]-1-(ethoxymethyl)pyrrole-3-carbonitrile.

19. The method according to claim 13 wherein the compound is applied to the plants or to the soil or water in which they are growing at a rate of about 0.1 kg/ha to 4.0 kg/ha.

20. A composition for controlling insects which comprises an agronomically acceptable carrier and an insecticidally effective amount of a compound having the structural formula

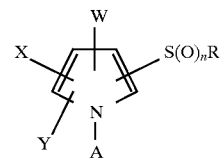

wherein A, R, W, X, Y and n are as described in claim 1.

21. The composition according to claim 20 wherein A, R, W, X, Y and n are as described in claim 2.

22. The composition according to claim 21 wherein the compound has the structural formula

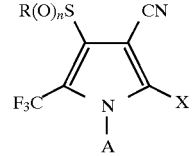

wherein

R and X are each independently phenyl optionally substituted with any combination of from one to three halogen, $NO_2$ or $CF_3$ groups;

n is an integer of 0, 1 or 2; and

A is hydrogen or $C_1$–$C_4$alkyl substituted with one $C_1$–$C_4$alkoxy group.

23. The composition according to claim 21 wherein the compound has the structural formula

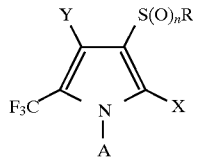

wherein

R and X are each independently phenyl optionally substituted with any combination of from one to three halogen, $NO_2$ or $CF_3$ groups;

n is an integer of 0, 1 or 2;

Y is Cl or Br; and

A is hydrogen or $C_1$–$C_4$alkyl substituted with one $C_1$–$C_4$alkoxy group.

24. The composition according to claim 21 wherein the compound has the structural formula

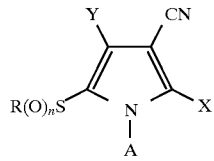

wherein

R and X are each independently phenyl optionally substituted with any combination of from one to three halogen, $NO_2$ or $CF_3$ groups;

n is an integer of 0, 1 or 2;

Y is hydrogen, Cl or Br; and

A is hydrogen or $C_1$–$C_4$alkyl substituted with one $C_1$–$C_4$alkoxy group.

* * * * *